US006855551B2

(12) United States Patent
Bawendi et al.

(10) Patent No.: US 6,855,551 B2
(45) Date of Patent: Feb. 15, 2005

(54) BIOLOGICAL APPLICATIONS OF QUANTUM DOTS

(75) Inventors: Moungi G. Bawendi, Boston, MA (US); Vikram C. Sundar, Stoneham, MA (US); Frederic V. Mikulec, La Jolla, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 216 days.

(21) Appl. No.: 09/832,959

(22) Filed: Apr. 12, 2001

(65) Prior Publication Data

US 2001/0023078 A1 Sep. 20, 2001

Related U.S. Application Data

(62) Division of application No. 09/160,454, filed on Sep. 24, 1998, now Pat. No. 6,326,144
(60) Provisional application No. 60/100,947, filed on Sep. 18, 1998.

(51) Int. Cl.[7] ............................................. G01N 33/543
(52) U.S. Cl. ..................... 436/6; 424/9.32; 424/9.34; 424/9.341; 424/9.36; 428/402; 428/402.24; 428/403; 428/404; 428/405; 428/406; 436/172; 436/173; 436/523; 436/524; 436/525; 436/527
(58) Field of Search ................................ 436/518, 523, 436/524, 525, 527, 136, 173; 424/9.32, 9.34, 9.341, 9.36; 428/402, 402.24, 403–406; 435/6

(56) References Cited

U.S. PATENT DOCUMENTS

| 5,293,050 A | 3/1994 | Chapple-Sokol et al. ..... 257/17 |
| 5,354,707 A | 10/1994 | Chapple-Sokol et al. ... 437/106 |
| 5,422,489 A | 6/1995 | Bhargava .................. 250/488.1 |
| 5,505,928 A | 4/1996 | Alivisatos et al. |
| 5,525,377 A | 6/1996 | Gallagher et al. ........... 427/512 |
| 5,751,018 A | 5/1998 | Alivisatos et al. |
| 5,985,353 A | 11/1999 | Lawton et al. |
| 5,990,479 A | 11/1999 | Weiss et al. |
| 6,423,551 B1 * | 7/2002 | Weiss et al. ................. 436/518 |

FOREIGN PATENT DOCUMENTS

| WO | WO 98/04740 | 2/1998 |
| WO | 98/19963 | 5/1998 |
| WO | WO 98/33070 | 7/1998 |

OTHER PUBLICATIONS

Matsumoto et al. (1996). Preparation of monodisperse CdS Nanocrystal by size selective Photocorrosion. J. Phys. Chem. 100(32):13781–13785.

Dabbousi et al. (1997). (CdSe)ZnS core–shell quantum–dots: synthesis and characterization of a size series of highly luminescent nanocrystal. J. Phys. Chem. B. 101:9463–9475.

Coffer et al. (1992). Characterization of quantum confined CdS nanocrystallites stabilized by deoxyribonucleic Acid (DNA). Nanotechnology. 3:69–76.

Mahtab et al. (1995). Protein–sized quantum dot luminescence can distinguish between "straight", "bent", and "kinked" oligonucletides. J. Am. Chem. Soc. 117:9099–9100.

(List continued on next page.)

*Primary Examiner*—Christopher L. Chin
(74) *Attorney, Agent, or Firm*—Steptoe & Johnson LLP

(57) ABSTRACT

The present invention provides a composition comprising fluorescent semiconductor nanocrystals associated to a compound, wherein the nanocrystals have a characteristic spectral emission, wherein said spectral emission is tunable to a desired wavelength by controlling the size of the nanocrystal, and wherein said emission provides information about a biological state or event.

40 Claims, 8 Drawing Sheets

OTHER PUBLICATIONS

Nirmal et al. (1996), Fluorescence intermittency in single cadmium selenide nanocrystals. Nature. 383:802–804.

Bawendi et al. (1992) Luminescence properties of CdSe quantum crystallites: resonance between interior and surface localized states. J. Chem. Phys. 96(2):946–954.

Correa–Duarte et al. (1998). Stabilization of CdS semiconductor nanoparticles against photodegradation by silica coating procedure. Chem. Phys. Lett. 286:497–501.

Norris et al. (1996). Measurement and assignment of the size–dependent optical spectrum in CdSe quantum dots. Physical Review B. 53(24):16338–16346.

Norris et al. (1996). Size dependence of exciton fine structure in CdSe quantum dots. Physical Review B, 53(24): 16347–16354.

Hines et al. (1996). Synthesis and characterization of strongly luminescing ZnS–Capped CdSe nanocrystals. J. Phys. Chem. 100:468–471.

Mahtab et al. (1996 Preferential adsorption of a "kinked" DNA to a neutral curved surface: comparisons to and implications for nonspecific DNA–protein interactions. J. Am. Chem Soc. 118:7028–7032.

Murphy et al. (1997) Quantum dots as inorganic DNA–binding proteins. Mat. Res. Soc. Symp. 452:597–600.

Lawless et al. (1995). Bifunctional capping of CdS nanoparticles and bridging to TiO2. J. Phys. Chem. 99:10329–10335.

Alivisatos (1996). Perspective on the physical chemistry of semiconductor nanocrystals. J. Phys. Chem. 100: 13226–13239.

Spanhel, et al., "Photochemistry of Colloidal Semiconductors. Surface Modification and Stability of Strong Luminescing CdS Particles," J. Am. Chem. Soc. 109(19):5649–5655, 1987.

Kortan, et al., "Nucleation of Growth of CdSe on ZnS Quantum Crystallite Seeds, and Vice Versa, in Inverse Micelle Media," J. Am. Chem. Soc. 112:1327–1332, 1990.

Coffer, et al., "Characterization of quantum–confined CdS Nanocrystallites stabilized by deoxyribonucleic acid (DNA)," Nanotechnology 3:69–76, 1992.

Murray, et al., "Synthesis and Characterization of Nearly Monodisperse CdE (E=S, Se, Te) Semiconductor Nanocrystallites," J. Am. Chem. Soc. 115(19):8706–8715, 1993.

Whitesell, et al., "Directionally Aligned Helical Peptides on Surfaces," Science 261:73–76, Jul. 1993.

Rajh, et al., "Synthesis and Characterization of Surface–Modified Colloidal CdTe Quantum Dots," J. Phys. Chem. 97:11999–12003, Nov. 1993.

Colvin, et al., "Light–emitting diodes made from cadmium selenide nanocrystals and a semiconducting polymer," Nature 370(6488):354–357, Aug. 4, 1994.

Lawless, et al., "Bifunctional Capping of CdS Nanoparticles and Bridging to TiO2," J. Phys. Chem. 99:10329–10335, 1995.

Dabbousi, et al., "Electroluminescence from CdSe quantum– dot/polymer composites," Appl. Phys. Lett. 66(11):1316–1318, Mar. 13, 1995.

Alivisatos, "Perspectives on the Physical Chemistry of Semiconductor Nanocrystals," J. Phys. Chem. 1996(100):13226–13239, 1996.

Danek, et al., "Synthesis of Luminescent Thin–Film CdSe/ZnSe Quantum Dot Composites Using CdSe Quantum Dots Passivated with an Overlayer of ZnSe," Chem. Mater. 8(1):173–180, 1996.

Liz–Marzan, et al., "Synthesis of Nanosized Gold–Silica Core–Shell Particles," Langmuir 12:4329–4335, 1996.

Matsumoto, et al., "Preparation of Monodisperse CdS Nanocrystals by Size Selection Photocorrosion," J. Phys. Chem 100(32):13781–13785, 1996.

Rogach, et al., "Synthesis and Characterization of Thiol–Stabilized CdTe Nanocrystals," Ber. Bunsenges. Phys. Chem. 100(11):1772–2778, 1996.

Hines, et al., "Synthesis and Characterization of Strongly Luminescing ZnS–Capped CdSe Nanocrystals," J. Phys. Chem. 100:468–471, Jan. 1996.

McGall, et al., "Light–directed synthesis of high–density oligonucleotide arrays using semiconductor photoresists," Proc. Natl. Acad. Sci. USA 93:13555–13560, Nov. 1996.

Chee, et al., "Accessing Genetic Information with High––Density DNA Arrays," Science 274(5287):610–614, Oct. 25, 1996.

Empedocles, et al., "Photoluminescence Spectroscopy of Single CdSe Nanocrystallite Quantum Dots," Phys. Rev. Lett. 77(18):3873–3876, Oct. 1996.

Nirmal, et al., "Fluorescence Intermittency in single Cadmium Selenide Nanocrystals," Nature 383:802–804, Oct. 1996.

Egner, et al., "Tagging in combinatorial chemistry: the use of coloured and fluorescent beads," Chem. Commun.:735–736, 1997.

Gan, et al., "Enhanced Photoluminescence and Characterization of Mn–Doped ZnS Nanocrystallites Synthesized in Microemulsion," Langmuir 1997 (13):6427–6431, 1997.

Empedocles, et al., "Quantum–Confined Stark Effect in Single CdSe Nanocrystallite Quantum Dots," Science 278:2114–2117, Dec. 1997.

Fodor, "Techwire," Science 277(5324):393–395, Jul. 18, 1997.

Kuno, et al., "The band edge luminescence of surface modified CdSe nanocrystallites: Probing the luminescing state," J. Chem. Phys. 106(23):9869–9882, Jun. 1997.

Dabbousi, et al., "(CdSe)ZnS core–shell quantum dots: synthesis and characterization of a size series of highly luminescent nanocrystallites," J. of Phys. Chem. B 101(46):9463–9475, Nov. 13, 1997.

Guha, et al., "Hybrid organic–inorganic semiconductor–based light–emitting diodes," J. Appl. Phys. 82(8):4126–4128, Oct. 15, 1997.

Fox, et al., "Fluorescence and Redox Activity of Probes Anchored through an Aminotrithiol to Polycrystalline Gold," Langmuir 14:816–820, 1998.

Mikulec, et al., "Fluorescent semiconductor nanocrystallites derivatized with biomolecules," Amer. Chem. Soc. Nat'l Meeting, Boston, MA, Aug. 24, 1998.

Service, "Semiconductor Beacons Light Up Cell Structures," Science 281:1930–1931, Sep. 25, 1998.

Jacoby, "Quantum dots meet biomolecules," C&E News:8, Sep. 28, 1998.

Bruchez, et al., "Semiconductor Nanocrystals as Fluorescent Biological Labels," Science 281:2013–2016, Sep. 1998.

Chan, et al., "Quantum Dot Bioconjugates for Ultrasensitive Nonisotopic Detection," Science 281:2016–2018, Sep. 1998.

Lett, "Color–Coding Quantum Dots Debut With Promising Careers In Clinical Diagnostics Field," :1–2, Sep. 25, 1998.

* cited by examiner

SINGLE-QUANTUM DOT LABELED IMMUNOASSAY

MULTI-QUANTUM DOT LABELED, PARALLEL IMMUNOASSAY

BIOLOGICAL APPLICATIONS OF QUANTUM DOTS

This application is a divisional of U.S. Ser. No. 09/160,454, filed on Sep. 24, 1998, now U.S. Pat. No. 6,326,144 which claims priority from provisional application U.S. Ser. No. 60/100,947, filed on Sep. 18, 1998, now abandoned, the entire contents of which are hereby incorporated by reference.

This application is related to the following applications that have been incorporated in their entirety by reference: Application U.S. Ser. No. 09/160,458 entitled "Inventory Control" filed Sep. 24, 1998 and application U.S. Ser. No. 09/156,863 entitled "Water-Soluble Luminescent Nanocrystals" filed on Sep. 18, 1998.

This invention was made with government support under Grant No. DMR-9400334 awarded by the National Science Foundation. The government has certain rights in the invention.

FIELD OF THE INVENTION

This invention relates to a composition comprising fluorescent semiconductor nanocrystals associated with compounds for use in biological applications.

BACKGROUND OF THE INVENTION

Traditional methods for detecting biological compounds in vivo and in vitro rely on the use of radioactive markers. For example, these methods commonly use radiolabeled probes such as nucleic acids labeled with $^{32}P$ or $^{35}S$ and proteins labeled with $^{35}S$ or $^{125}I$ to detect biological molecules. These labels are effective because of the high degree of sensitivity for the detection of radioactivity. However, many basic difficulties exist with the use of radioisotopes. Such problems include the need for specially trained personnel, general safety issues when working with radioactivity, inherently short half-lives with many commonly used isotopes, and disposal problems due to full landfills and governmental regulations. As a result, current efforts have shifted to utilizing non-radioactive methods of detecting biological compounds. These methods often consist of the use of fluorescent molecules as tags (e.g. fluorescein, ethidium, methyl coumarin, rhodamine, and Texas red), or the use of chemiluminescence as a method of detection. Presently however, problems still exist when using these fluorescent and chemiluminescent markers. These problems include photobleaching, spectral separation, low fluorescence intensity, short half-lives, broad spectral linewidths, and non-gaussian asymmetric emission spectra having long tails.

Fluorescence is the emission of light resulting from the absorption of radiation at one wavelength (excitation) followed by nearly immediate reradiation usually at a different wavelength (emission). Fluorescent dyes are frequently used as tags in biological systems. For example, compounds such as ethidium bromide, propidium iodide, Hoechst dyes, and DAPI (4',6-diamindino-2-phenylindole) interact with DNA and fluoresce to visualize DNA. Other biological components can be visualized by fluorescence using techniques such as immunofluorescence which utilizes antibodies labeled with a fluorescent tag and directed at a particular cellular target. For example, monoclonal or polyclonal antibodies tagged with fluorescein or rhodamine can be directed to a desired cellular target and observed by fluorescence microscopy. An alternate method uses secondary antibodies that are tagged with a fluorescent marker and directed to the primary antibodies to visualize the target.

Another application of fluorescent markers to detect biological compounds is fluorescence in situ hybridization (FISH). This method involves the fluorescent tagging of an oligonucleotide probe to detect a specific complementary DNA or RNA sequence. An alternative approach is to use an oligonucleotide probe conjugated with an antigen such as biotin or digoxygenin and a fluorescently tagged antibody directed toward that antigen to visualize the hybridization of the probe to its DNA target. FISH is a powerful tool for the chromosomal localization of genes whose sequences are partially or fully known. Other applications of FISH include in situ localization of mRNA in tissues samples and localization of non-genetic DNA sequences such as telomeres.

Fluorescent dyes also have applications in non-cellular biological systems. For example, the advent of fluorescently-labeled nucleotides has facilitated the development of new methods of high-throughput DNA sequencing and DNA fragment analysis (ABI system; Perkin-Elmer, Norwalk, Conn.). DNA sequencing reactions that once occupied four lanes on DNA sequencing gels can now be analyzed simultaneously in one lane. Briefly, four reactions are performed to determine the positions of the four nucleotide bases in a DNA sequence. The DNA products of the four reactions are resolved by size using polyacrylamide gel electrophoresis. With singly radiolabeled ($^{32}P$ or $^{35}S$) DNA, each reaction is loaded into an individual lane. The resolved products result in a pattern of bands that indicate the identity of a base at each nucleotide position. This pattern across four lanes can be read like a simple code corresponding to the nucleotide base sequence of the DNA template. With fluorescent dideoxynucleotides, samples containing all four reactions can be loaded into a single lane. Resolution of the products is possible because each sample is marked with a different colored fluorescent dideoxynucleotide. For example, the adenine sequencing reaction can be marked with a green fluorescent tag and the other three reactions marked with different fluorescent colors. When all four reactions are analyzed in one lane on a DNA sequencing gel, the result is a ladder of bands consisting of four different colors. Each fluorescent color corresponds to the identity of a nucleotide base and can be easily analyzed by automated systems.

There are chemical and physical limitations to the use of organic fluorescent dyes. One of these limitations is the variation of excitation wavelengths of different colored dyes. As a result, simultaneously using two or more fluorescent tags with different excitation wavelengths requires multiple excitation light sources. This requirement thus adds to the cost and complexity of methods utilizing multiple fluorescent dyes.

Another drawback when using organic dyes is the deterioration of fluorescence intensity upon prolonged exposure to excitation light. This fading is called photobleaching and is dependent on the intensity of the excitation light and the duration of the illumination. In addition, conversion of the dye into a nonfluorescent species is irreversible. Furthermore, the degradation products of dyes are organic compounds which may interfere with biological processes being examined.

Another drawback of organic dyes is the spectral overlap that exists from one dye to another. This is due in part to the relatively wide emission spectra of organic dyes and the overlap of the spectra near the tailing region. Few low molecular weight dyes have a combination of a large Stokes shift, which is defined as the separation of the absorption and emission maxima, and high fluorescence output. In addition, low molecular weight dyes may be impractical for some applications because they do not provide a bright enough fluorescent signal. The ideal fluorescent label should fulfill many requirements. Among the desired qualities are the following: (i) high fluorescent intensity (for detection in small quantities), (ii) a separation of at least 50 nm between the absorption and fluorescing frequencies, (iii) solubility in water, (iv) ability to be readily linked to other molecules, (v) stability towards harsh conditions and high temperatures, (vi) a symmetric, nearly gaussian emission lineshape for easy deconvolution of multiple colors, and (vii) compatibility with automated analysis. At present, none of the conventional fluorescent labels satisfies all these requirements. Furthermore, the differences in the chemical properties of standard organic fluorescent dyes make multiple, parallel assays quite impractical since different chemical reactions may be involved for each dye used in the variety of applications of fluorescent labels.

SUMMARY OF THE INVENTION

The present invention provides a composition that can provide information about a biological state or event. The composition by way of example can detect the presence or amounts of a biological moiety; the structure, composition, and conformation of a biological moiety; the localization of a biological moiety in an environment; interactions of biological moieties; alterations in structures of biological compounds; and alterations in biological processes.

The composition is comprised of a fluorescent semiconductor nanocrystal (known as a quantum dot) having a characteristic spectral emission, which is tunable to a desired energy by selection of the particle size of the quantum dot. The composition further comprises a compound, associated with the quantum dot that has an affinity for a biological target. The composition interacts or associates with a biological target due to the affinity of the compound with the target. Location and nature of the association can be detected by monitoring the emission of the quantum dot.

In operation, the composition is introduced into an environment containing a biological target and the composition associates with the target. The composition:target complex may be spectroscopically viewed by irradiation of the complex with an excitation light source. The quantum dot emits a characteristic emission spectrum which can be observed and measured spectrophotometrically.

As an advantage of the composition of the present invention, the emission spectra of quantum dots have linewidths as narrow as 25–30 nm depending on the size heterogeneity of the sample, and lineshapes that are symmetric, gaussian or nearly gaussian with an absence of a tailing region. The combination of tunability, narrow linewidths, and symmetric emission spectra without a tailing region provides for high resolution of multiply-sized quantum dots within a system and enables researchers to examine simultaneously a variety of biological moieties tagged with QDs.

In addition, the range of excitation wavelengths of the nanocrystal quantum dots is broad and can be higher in energy than the emission wavelengths of all available quantum dots. Consequently, this allows the simultaneous excitation of all quantum dots in a system with a single light source, usually in the ultraviolet or blue region of the spectrum. QDs are also more robust than conventional organic fluorescent dyes and are more resistant to photobleaching than the organic dyes. The robustness of the QD also alleviates the problem of contamination of the degradation products of the organic dyes in the system being examined. Therefore, the present invention provides uniquely valuable tags for detection of biological molecules and the interactions they undergo.

In one preferred embodiment, the composition comprises quantum dots associated with molecules that can physically interact with biological compounds. Without limiting the scope of the invention, molecules include ones that can bind to proteins, nucleic acids, cells, subcellular organelles, and other biological molecules. The compound used in the composition of the present invention preferably has an affinity for a biological target. In some preferred embodiments, the compound has a specific affinity for a biological target. The affinity may be based upon any inherent properties of the compound, such as without limitation, van der Waals attraction, hydrophilic attractions, ionic, covalent, electrostatic or magetic attraction of the compound to a biological target. As used herein, "biological target" is meant any moiety, compound, cellular or subcellular component which is associated with biological functions. The biological target includes without limitation proteins, nucleic acids, cells, subcellular organelles and other biological moieties.

In another preferred embodiment, the composition comprises quantum dots associated with proteins. Without limiting the scope of the invention, the proteins may be antibodies that are directed towards specific biological antigens such as other proteins, nucleic acids, subcellular organelles, and small molecules that are conjugated to biological compounds. The proteins may also be proteins that interact specifically or non-specifically with other biological compounds.

In another preferred embodiment, the composition comprises quantum dots associated with nucleic acids. Without limiting the scope of the invention, the nucleic acids may be oligonucleotides or deoxyribooligonucleotides that hybridize to nucleic acid polymers in vivo or in vitro. The nucleic acids may also be nucleotides, deoxynucleotides, dideoxynucleotides, or derivatives and combinations thereof that are used for the synthesis of DNA or RNA.

In another aspect of the invention, a method of detecting biological compounds using quantum dots is provided.

DEFINITIONS

Quantum dots are a semiconductor nanocrystal with size-dependent optical and electronic properties. In particular, the band gap energy of a quantum dot varies with the diameter of the crystal.

DNA is deoxyribonucleic acid.

Monodispersed particles are defined as having at least 60% of the particles fall within a specified particle size range. Monodispersed particles deviate less than 10% in rms diameter and preferably less than 5%.

Quantum yield is defined as the ratio of photons emitted to that absorbed.

A small molecule is defined as an organic compound either synthesized in the laboratory or found in nature. Typically, a small molecule is characterized in that it contains several carbon-carbon bonds, and has a molecular weight of less than 1500 grams/Mol A biological state is defined as the quantitative and qualitative presence of a biological moiety; the structure, composition, and conformation of a biological moiety; and the localization of a biological moiety in an environment.

Biological events are defined as interactions of biological moieties, biological processes, alterations in structures of biological compounds, and alterations in biological processes.

DETAILED DESCRIPTION OF THE INVENTION

Figure 1:
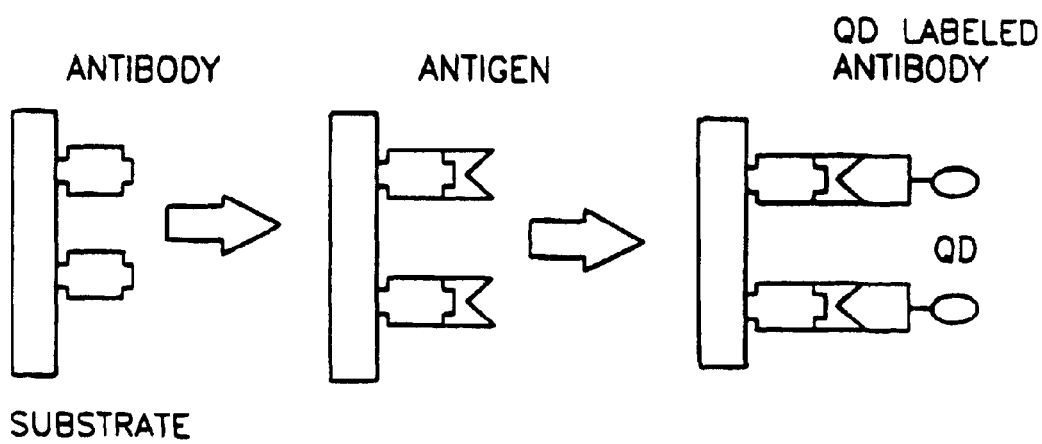
FIG. 1 is a cartoon depiction of the single-sized quantum dot preparation labeled immunoassay.

The present invention provides a composition comprising semiconductor nanocrystals (also referred to in this application as quantum dots; QDs) as fluorescent tags associated with a reagent or molecule wherein the composition can detect the presence or amount of a biological molecule, detect biological interactions, detect biological processes, detect alterations in biological processes, or detect alterations in the structure of a biological compound.

Semiconductor nanocrystals (quantum dots) demonstrate quantum confinement effects in their luminescent properties. When quantum dots are illuminated with a primary energy source, a secondary emission of energy occurs of a frequency that corresponds to the band gap of the semiconductor material used in the quantum dot. In quantum confined particles, the band gap is a function of the size of the nanocrystal.

Many semiconductors that are constructed of elements from groups II–VI, III–V and IV of the periodic table have been prepared as quantum sized particles, exhibit quantum confinement effects in their physical properties, and can be used in the composition of the invention. Exemplary materials suitable for use as quantum dots include ZnS, ZnSe, ZnTe, CdS, CdSe, CdTe, GaN, GaP, GaAs, GaSb, InP, InAs, InSb, AlS, AlP, AlAs, AlSb, PbS, PbSe, Ge, and Si and ternary and quaternary mixtures thereof. The quantum dots may further include an overcoating layer of a semiconductor having a greater band gap.

The semiconductor nanocrystals are characterized by their uniform nanometer size. By "nanometer" size, it is meant less than about 150 Angstroms (Å), and preferably in the range of 12–150 Å. The nanocrystals also are substantially monodisperse within the broad nanometer range given above. By monodisperse, as that term is used herein, it is meant a colloidal system in which the suspended particles have substantially identical size and shape. For the purposes of the present invention, monodisperse particles mean that at least 60% of the particles fall within a specified particle size range. Monodisperse particles deviate less than 10% in rms diameter, and preferably less than 5%.

The narrow size distribution of the quantum dots allows the possibility of light emission in narrow spectral widths. Monodisperse quantum dots have been described in detail in Murray et al. (*J. Am. Chem. Soc.*, 115:8706 (1993)); in the thesis of Christopher Murray, "Synthesis and Characterization of II–VI Quantum Dots and Their Assembly into 3-D Quantum Dot Superlattices", Massachusetts Institute of Technology, September, 1995; and in U.S. patent application Ser. No. 08/969,302 entitled "Highly Luminescent Color-selective Materials" which are hereby incorporated in their entireties by reference.

The fluorescence of semiconductor nanocrystals results from confinement of electronic excitations to the physical dimensions of the nanocrystals. In contrast to the bulk semiconductor material from which these dots are synthesized, these quantum dots have discrete optical transitions, which are tunable with size (U.S. patent application Ser. No. 08/969,302 entitled "Highly Luminescent Color-selective Materials"). Current technology allows good control of their sizes (between 12 to 150 Å; standard deviations approximately 5%), and thus, enables construction of QDs that emit light at a desired wavelength throughout the UV-visible-IR spectrum with a quantum yield ranging from 30–50% at room temperature in organic solvents and 10–30% at room temperature in water.

The present invention provides a composition comprising semiconductor nanocrystals (quantum dots) associated with a reagent or molecule such that the composition can detect the presence and amounts of biological compounds, detect interactions in biological systems, detect biological processes, detect alterations in biological processes, or detect alterations in the structure of biological compounds. Without limitation to the present invention, these reagents or molecules include any molecule or molecular complex that can interact with a biological target, molecules or molecular complexes that can associate with biological targets to detect biological processes, or reactions, and molecules or molecular complexes that can alter biological molecules or processes. Preferably, the molecules or molecular complexes physically interact with biological compounds. Preferably, the interactions are specific. The interactions can be, but are not limited to, covalent, noncovalent, hydrophobic, hydrophilic, electrostatic, van der Waals, or magnetic. Preferably, these molecules are small molecules, proteins, or nucleic acids or combinations thereof.

Quantum dots (QDs) are capable of fluorescence when excited by light. Currently, detection of biological compounds by photoluminescence utilizes fluorescent organic dyes and chemiluminescent compounds. The use of QDs as fluorescent markers in biological systems provides advantages over existing fluorescent organic dyes. Many of these advantages relate to the spectral properties of QDs. For example without limiting the scope of the present invention, the ability to control the size of QDs enables one to construct QDs with fluorescent emissions at any wavelength in the UV-visible-IR region. Therefore, the colors (emissions) of QDs are tunable to any desired spectral wavelength. Furthermore, the emission spectra of monodisperse QDs have linewidths as narrow as 25–30 nm. The linewidths are dependent on the size heterogeneity of QDs in each preparation. Single quantum dots have been observed to have FWHMs of 12–15 nm. In addition, QDs with larger FWHM in the range of 40–60 nm can be readily made and have the same physical characteristics, such as emission wavelength tunability and excitation in the UV-blue, preferably in the blue region of the spectrum, as QDs with narrower FWHM.

The narrow spectral linewidths and nearly gaussian symmetrical lineshapes lacking a tailing region observed for the emission spectra of QDs combined with the tunability of the emission wavelengths of QDs allows high spectral resolution in a system with multiple QDs. In theory, up to 10–20 different-sized QDs from different preparations of QDs, with each sample having a different emission spectrum, can be used simultaneously in one system with the overlapping spectra easily resolved using deconvolution software.

Another advantage to the use of QDs as fluorescent markers over existing organic fluorescent dyes is that only a single light source (usually in the UV-blue, and preferably in the blue region of the spectrum) is needed to excited all QDs in a system. Organic dyes with different emission wavelengths usually have different excitation wavelengths. Thus, multiple light sources or a single light source with adaptable light-filters are needed for systems that utilize organic dyes with different excitation wavelength. Since all QDs of the present invention can be excited by light in the UV-blue region of the spectrum (preferably the blue visible region), a single light source can be used. This minimizes the technical complexity needed to provide an excitation light source. In addition, by using blue light, the source radiation will not interfere with any of the fluorescence measurements taken in the visible or infrared region of the light spectrum, and also will not damage biological molecules. For example, UV light can cause dimerization in DNA molecules.

Another advantage of the use of QDs over organic fluorescent dyes that are currently available is the robust nature of the QDs due to their crystalline inorganic structure and their protective overcoating layer. These QDs are more resistant to photobleaching than what is observed for organic dyes. Also, since QDs described in the application are composed of similar materials and are protected by the same organic capping groups, chemical uniformity of QDs allows the extrapolation of a protocol developed to attach one particular size of QDs to a molecule to QDs of all sizes within that class of QDs. Such uniformity should be valuable in extending conventional assaying techniques to include parallel detection schemes. Therefore, the present invention provides a series of fluorescent probes, which span the spectrum from the UV to the IR, and also can have substantially identical chemical properties.

Because detection of biological compounds is most preferably carried out in aqueous media, a preferred embodiment of the present invention, utilizes quantum dots that are solubilized in water. Quantum dots described by Bawendi et al. (*J. Am. Chem. Soc.*, 115:8706, 1993) are soluble or dispersible only in organic solvents, such as hexane or pyridine. It is preferred that the QDs are water-soluble and associated with molecules capable of interacting with biological compounds. However,

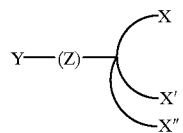

construction of water-soluble QDs suitable for biological systems (U.S. Patent Application entitled "Water-Soluble Luminescent Nanocrystals" incorporated herein by reference and filed on Sep. 18, 1998).

An water-solubilizing layer is found at the outer surface of the overcoating layer. The outer layer includes a compound having at least one linking group for attachment of the compound to the overcoating layer and at least one hydrophilic group spaced apart from the linking group by a hydrophobic region sufficient to prevent electron charge transfer across the hydrophobic region. The affinity for the nanocrystal surface promotes coordination of the linking moiety to the quantum dot outer surface and the moiety with affinity for the aqueous medium stabilizes the quantum dot suspension.

Without limitation to the scope of the present invention, the compound may have the formula, $H_zX((CH_2)_nCO_2H)_y$ and salts thereof, where X is S, N, P or O=P; $n \geq 6$; and z and y are selected to satisfy the valence requirements of X. Exemplary compound for use in the invention may have the formula,

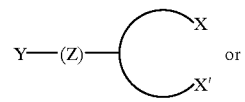

where X, X' and X" are the same or different and are selected from the group of S, N, P or O=P; Y is a hydrophilic moiety; and Z is a hydrophobic region having a backbone of at least six atoms. X, X' and X" may include other substituents in order to satisfy the valence requirements, such as for example, amines, thiols, phosphines and phosphine oxides, substituted by hydrogen or other organic moieties. In addition, the atoms bridging X, X' and X" are selected to form a 5-membered to 8-membered ring upon coordination to the semiconductor surface. The bridging atoms are typically carbon, but may be other elements, such as oxygen, nitrogen, and sulfur. Y may be any charged or polar group, such as carboxylates, sulfonates, phosphates, polyethylene glycol and ammonium salt, and the like. Z is typically an alkyl group or alkenyl group, but may also include other atoms, such as carbon and nitrogen. Z may be further modified as described herein to provide attractive interactions with neighboring ligands.

In a particular preferred embodiment, the hydrophilic moiety X also provides a reactive group capable of a reaction to couple the compound to the quantum dot. For example, where the hydrophilic moiety is a —COOH or a —COO group, it may be used to couple a variety of biological compounds to form a corresponding ester, amide, or anhydride. By way of the example only, a carboxylic acid terminated QDs can react with an amino acid to form an amide coupling. The amide may function as the compound having affinity for a biological target.

In other preferred embodiments, a water-soluble QD is provided in which the outer layer has been partially substituted by a ligand which terminates in a reactive group. The reactive group is not selected for its hydrophilic properties but rather for its ability to couple with the compound of the invention. Exemplary reactive groups include carboxylic acid groups, thiol groups and amine groups.

In yet another embodiment of the invention, a water-soluble QD is provided in which the outer layer is partially substituted by a ligand which comprises the compound of the invention. By way of example only, the compound may include a parent group terminating in a thiol, amine or phosphine or phosphine oxide, which can interact directly with the semiconductor nanocrystal surface.

In one preferred embodiment, the present invention provides a composition comprising a semiconductor nanocrystal that emits light at a tunable wavelength and is associated with a protein. Without limitation to the scope of the invention, the protein can be a peptide or an amino acid or derivatives thereof. Without limiting the scope of the invention since alternative methods may be utilized to acheive the same results, the QDs may be associated with amino acids and peptides through conjugation of an amino acid residue with carboxylic acid groups conjugated with N-hydroxysuccinimide (NHS) on the surface of the QDs. In a preferred embodiment, the quantum dots are water-soluble, and as described in Example 4, creating the water-soluble quantum dots involves covering the surface of the dots with hydrophilic moieties such as carboxylic acid groups (U.S. patent application entitled "Water-Soluble Fluorescent Nanocrystals"). Carboxylic acid groups can be conjugated with N-hydroxysuccinimide (NHS) to activate the carbonyl group for further conjugation with an amino acid residue such as lysine.

As an example without limitation to the present invention, the composition comprises quantum dots associated with a protein that is an antibody. The antibody can be a polyclonal or a monoclonal antibody. Antibodies tagged with QDs as fluorescent markers of one color or of multiple colors can then be used in applications such as immunochemistry and immunocytochemistry.

As another example without limitation to the present invention, the composition comprises QDs conjugated to proteins with desired binding characteristics such as specific binding to another protein (e.g. receptors), binding to ligands (e.g. cAMP, signaling molecules) and binding to nucleic acids (e.g. sequence-specific binding to DNA and/or RNA).

In another preferred embodiment, the present invention provides a composition comprising a semiconductor nanocrystal that emits light at a tunable wavelength and is associated with a molecule or molecular complex that is capable of interacting with a biological compound. As an example without limiting the scope of the invention, QDs can be conjugated to molecules that can interact physically with biological compounds such as cells, proteins, nucleic acids, subcellular organelles and other subcellular components. For example, QDs can be associated with biotin which can bind to the proteins, avidin and streptavidin. Also, QDs can be associated with molecules that bind non-specifically or sequence-specifically to nucleic acids (DNA RNA). As examples without limiting the scope of the invention, such molecules include small molecules that bind to the minor groove of DNA (for reviews, see Geierstanger and Wemmer. *Annu Rev Biophys Biomol Struct*. 24:463–493, 1995; and Baguley. *Mol Cell Biochem*. 43(3):167–181, 1982), small molecules that form adducts with DNA and RNA (e.g. CC-1065, see Henderson and Hurley. *J Mol Recognit*. 9(2): 75–87, 1996; aflatoxin, see Garner. *Mutat Res*. 402(1–2): 67–75, 1998; cisplatin, see Leng and Brabec. *IARC Sci Publ*. 125:339–348, 1994), molecules that intercalate between the base pairs of DNA (e.g. methidium, propidium, ethidium, porphyrins, etc. for a review see Bailly, Henichart, Colson, and Houssier. *J Mol Recognit*. 5(4): 155–171, 1992), radiomimetic DNA damaging agents such as bleomycin, neocarzinostatin and other enediynes (for a review, see Povirk. *Mutat Res*. 355(1–2):71–89, 1996), and metal complexes that bind and/or damage nucleic acids through oxidation (e.g. Cu-phenanthroline, see Perrin, Mazumder, and Sigman. *Prog Nucleic Acid Res Mol Biol*. 52:123–151, 1996; Ru(II) and Os(II) complexes, see Moucheron, Kirsch-De Mesmaeker, and Kelly. *J Photochem Photobiol B*, 40(2) :91–106, 1997; chemical and photochemical probes of DNA, see Nielsen, *J Mol Recognit*, 3(1):1–25, 1990).

Molecules and higher order molecular complexes (e.g. polymers, metal complexes) associated with QDs can be naturally occurring or chemically synthesized. Molecules or higher order molecular complexes can be selected to have a desired physical, chemical or biological property. Such properties include, but are not limited to, covalent and noncovalent association with proteins, nucleic acids, signaling molecules, procaryotic or eukaryotic cells, viruses, subcellular organelles and any other biological compounds. Other properties of such molecules, include but are not limited to, the ability to affect a biological process (e.g. cell cycle, blood coagulation, cell death, transcription, translation, signal transduction, DNA damage or cleavage, production of radicals, scavenging radicals, etc.), and the ability to alter the structure of a biological compound (e.g. crosslinking, proteolytic cleavage, radical damage, etc.). In addition, molecules and higher order molecular complexes associated with QDs may have more general physical, chemical or biological properties such as, but not limited to, hydrophobicity, hydrophilicity, magnetism and radioactivity.

In another preferred embodiment, the present invention provides a composition comprising a semiconductor nanocrystal that emits light at a tunable wavelength and is associated with a nucleic acid. The association can be direct or indirect. The nucleic acid can be any ribonucleic acid, deoxyribonucleic acid, dideoxyribonucleic acid, or any derivatives and combinations thereof. The nucleic acid can also be oligonucleotides of any length. The oligonucleotides can be single-stranded, double-stranded, triple-stranded or higher order configurations (e.g. Holliday junctions, circular single-stranded DNA, circular double-stranded DNA, DNA cubes, (see Seeman. *Annu Rev Biophys Biomol Struct*. 27:225–248, 1998)).

Without limiting the scope of the present invention, QDs can be associated with individual nucleotides, deoxynucleotides, dideoxynucleotides or any derivatives and combinations thereof and used in DNA polymerization reactions such as DNA sequencing, reverse transcription of RNA into DNA, and polymerase chain reactions (PCR). Nucleotides also include monophosphate, diphosphate and triphophates and cyclic derivatives such as cyclic adenine monophosphate (cAMP). Other uses of QDs conjugated to nucleic acids included fluorescence in situ hybridization (FISH). In this preferred embodiment, QDs are conjugated to oligonucleotides designed to hybridize to a specific sequence in vivo. Upon hybridization, the fluorescent QD tags are used to visualize the location of the desired DNA sequence in a cell. For example, the cellular location of a gene whose DNA sequence is partially or completely known can be determined using FISH. Any DNA or RNA whose sequence is partially or completely known can be visually targeted using FISH. For example without limiting the scope of the present invention, messenger RNA (mRNA), DNA telomeres, other highly repeated DNA sequences, and other non-coding DNA sequencing can be targeted by FISH.

In another preferred embodiment, the present invention provides a composition comprising fluorescent quantum dots associated with a molecule or reagent for detection of biological compounds such as enzymes, enzyme substrates, enzyme inhibitors, cellular organelles, lipids, phospholipids, fatty acids, sterols, cell membranes, molecules involved in signal transduction, receptors and ion channels. The composition also can be used to detect cell morphology and fluid flow; cell viability, proliferation and function; endocytosis and exocytosis; and reactive oxygen species (e.g. superoxide, nitric oxide, hydroxyl radicals, oxygen radicals.) In addition, the composition can be used to detect hydrophobic or hydrophilic regions of biological systems.

Other applications of fluorescent markers in biological systems can be found in Haugland, R. P. *Handbook of Fluorescent Probes and Research Chemicals* (Molecular Probes. Eugene, Oreg. Sixth Ed. 1996; Website, www.probes.com) which is incorporated by reference in its entirety.

In another aspect of the invention, the present invention provides methods of detecting biological compounds using QDs. Without limiting the scope of the present invention, the conjugation of QDs to such molecules as small molecules, proteins, and nucleic acids allows the use of QDs in any method of detecting the presence or amount of biological compounds. Certain particular methods are discussed below in order to highlight the advantages and utilities of the inventive compositions. These methods, include but are not limited to, fluorescence immunocytochemistry, fluorescence microscopy, DNA sequence analysis, fluorescence in situ hybridization (FISH), fluorescence resonance energy transfer (FRET), flow cytometry (Fluorescence Activated Cell Sorter; FACS) and diagnostic assays for biological systems.

Immunocytochemistry

Currently, fluorescence immunocytochemistry combined with fluorescence microscopy allows researchers to visualize biological moieties such as proteins and nucleic acids within a cell (see *Current Protocols in Cell Biology*, John Wiley & Sons, Inc., New York; incorporated herein by reference). One method uses primary antibodies hybridized to the desired in vivo target. Then, secondary antibodies conjugated with fluorescent dyes and targeted to the primary antibodies are used to tag the complex. The complex is visualized by exciting the dyes with a wavelength of light matched to the dye's excitation spectrum. Fluorescent dyes that interact with nucleic acids such as DAPI (4',6-diamindino-2-phenylindole), propidium iodide, ethidium bromide and Hoechst dyes are used to visual DNA and RNA.

Fluorescent tags are also used to detect the presence and location of specific nucleic acid sequences. DNA sequences that are complementary to the target sequences are directly labeled with fluorescent nucleotides (e.g. fluorescein-12-dUTP) and used as probes to visualize the presence and location of the target nucleotide sequence. Examples of targets include messenger RNA and genomic DNA. Alternatively, the DNA probe can be labeled with a marker such as biotin or digoxygenin. Upon hybridization of the probe to its target sequence, a fluorescent-conjugated antibody raised against the marker (e.g. biotin or digoxygenin) is used to locate and visualize the probe.

Colocalization of biological moieties in a cell is performed using different sets of antibodies for each cellular target. For example, one cellular component can be targeted with a mouse monoclonal antibody and another component with a rabbit polyclonal antibody. These are designated as the primary antibody. Subsequently, secondary antibodies to the mouse antibody or the rabbit antibody, conjugated to different fluorescent dyes having different emission wavelengths, are used to visualize the cellular target. In addition, fluorescent molecules such as DAPI (4',6-diamidino-2-phenylindole) can target and stain biological moieties directly. An ideal combination of dyes for labeling multiple components within a cell would have well-resolved emission spectra. In addition, it would be desirable for this combination of dyes to have strong absorption at a coincident excitation wavelength.

Tunable nanocrystal quantum dots are ideal for use in fluorescence immunocytochemistry. The absorption spectra of QDs are broad. As a result, a single light source (in the UV-blue region, preferably in the blue region) can be used to excite all QDs in a system simultaneously. This allows a researcher to visualize the location of all QDs (and thus the biological components targeted) in a cell simultaneously. In addition, a single excitation light source simplifies the machinery involved in fluorescence excitation. Furthermore, the combination of narrow linewidths, and symmetrical, nearly gaussian lineshapes lacking a tailing region in the emission spectra of QDs and the tunability of the emission wavelengths allows the use of multiple QD tags in one system. As a result, as many as 10–20 differently sized QDs, each with different a emission spectrum, can be used simultaneously in one system and more easily resolved with the use of deconvolution software.

Immunoassay

One protocol for using QDs in heterogeneous immunoassays (assays in which the excess antibodies have to be removed in a separate step) is described in FIG. 1. An antibody to an antigen is adsorbed or covalently linked to a solid phase (see *Current Protocols in Immunology*, John Wiley & Sons, Inc., New York; incorporated herein by reference). Then the antigen is added and allowed to bind to the solid-phase antibody. After the excess antigen is removed, the matrix is reacted with QD-labeled antibody. After a second wash, the fluorescence can be quantified.

Figure 2:
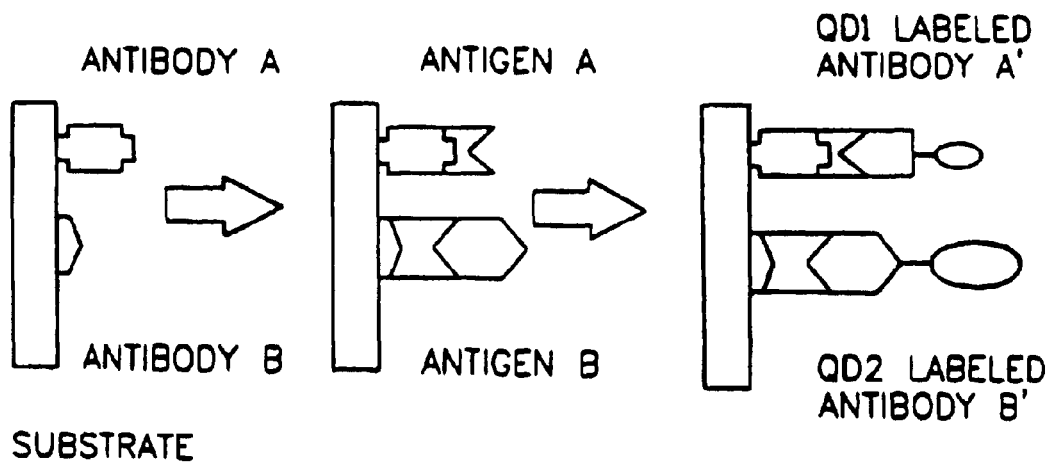
FIG. 2 is a cartoon depiction of the multicolored quantum dot labeled, parallel immunoassay.

This protocol is amenable to multiple, parallel immunoassaying schemes as well (FIG. 2). A series of different antibodies is covalently linked to a substrate. Then disparate antibody specific antigens can be bound to this array. Finally, different antibodies labeled with specific-size QDs are bound to the antigens. Again, the fluorescence from each size QD can be quantified and the relative amount of each antigen determined. Such an extension should be possible as different sized QDs not only have similar solubility properties, narrow linewidths and unique, size-dependent fluorescence frequencies, but also can be excited by the same source of radiation (in the UV-blue, preferably in the blue region of the spectrum).

High-Throughput DNA Sequence Analyses

QDs conjugated to nucleic acids have applications in non-cellular biological systems. As an example without limiting the scope of the invention, with the advent of fluorescently-labeled nucleotides, high-throughput DNA sequencing and DNA fragment analysis have become powerful tools in the analyses of DNA sequences (ABI system; Perkin-Elmer).

To describe these sequencing reactions briefly, four reactions are performed to determine the positions of the four nucleotide bases within a DNA sequence. Using a DNA sample as a template, a chain of DNA is synthesized from a pool of nucleotides containing the four deoxynucleotides and one additional dideoxynucleotide. For example, in the adenine sequencing reaction, DNA is synthesized from a mixture that includes all four deoxynucleotides (dATP, dGTP, dCTP, dTTP) plus dideoxyadenosine triphosphate (ddATP). The enzyme DNA polymerase will synthesize the new chain of DNA by linking dNTPs. Occasionally DNA polymerase will incorporate a ddATP instead of a dATP. The ddATP in the nascent chain will then terminate the synthesis of that chain of DNA due to the lack of the 3' hydroxyl group as a connection to the next dNTP. Thus the DNA products from the adenine sequencing reaction will be a heterogenous mixture of DNA that vary in length with each chain terminated at a position corresponding to adenine.

The four DNA sequencing reactions are resolved by size by polyacrylamide gel electrophoresis. With singly radiolabeled ($^{32}$P or $^{35}$S) DNA, the four reactions are loaded into four individual lanes. The resolved products of differing sizes result in a pattern of bands that indicate the identity of a base at each nucleotide position. This pattern across the four lanes can be read like a simple code corresponding to the nucleotide base sequence of the DNA template. With fluorescent dideoxynucleotides, samples containing all four dideoxynucleotide chain-terminating reactions can be loaded into a single lane. Resolution of the four dideoxynucleotide reactions is possible because of the different fluorescent labels for each sample. For example, ddATP can be conjugated with a green fluorescent tag. The other three ddNTP (dideoxynucleotide triphosphate) are tagged with three different fluorescent colors. Thus, each chain-terminating ddNTP is coded with a different color. When all four reactions are resolved in one lane on a DNA sequencing gel, the result is one ladder of bands having four different colors. Each fluorescent color corresponds to the identity of the nucleotide base and can be easily analyzed by automated systems. However as previously discussed, multiple light sources are needed for excitation of the four different fluorescent markers. The use of QDs as the fluorescent tags for each dideoxynucleotide chain-terminating reaction simplifies the automation of high-throughput DNA sequencing since only a single light source is needed to excite all four fluorescent tags.

In PCR (polymerase chain reaction)-based DNA typing and identification, short tandem repeat (STR) loci in the human genome are amplified by PCR using primers that are labeled with fluorescent tags. The size of these loci can differ or can coincide from person to person and depends on genetic differences in the population. Usually multiple loci are examined. Any locus that shows a size difference with another sample conclusively indicates that the two samples are derived from two different individuals. However, demonstrating that two samples originate from the same individual is less conclusive. Unlike fingerprint patterns, the size of STR loci can coincide between two individuals. However, the statistical probability of multiple loci coinciding in size between two individuals decreases as the number of loci examined is increased. Using conventional organic fluorescent dyes, a limitation to the number of samples resolved in a single lane (and thus high-throughput) is the number of the fluorescent tags available and the resolution of the emission spectra. Increasing the resolution of the fluorescent tags thus would increase the capacity of the number of loci tested per lane on a gel.

Fluorescence Resonance Energy Transfer (FRET)

The present invention provides a method for detecting the proximity of two or more biological compounds. Long-range resonance energy transfer between QDs and between a QD and an organic fluorescent dye can occur efficiently if the spacing between them is less than approximately 100 Å. This long-range effect can be exploited to study biological systems. In particular, this effect can be used to determine the proximity of two or more biological compounds to each other. Conversely, this effect can be used to determine that two or more biological compounds are not in proximity to each other. Advantages to using QDs combined with organic dyes for FRET include the ability to tune the narrow emission of the QDs to match precisely the excitation wavelength of organic dyes, thus reducing background signals.

In a preferred embodiment, QDs can be conjugated to a biological compound or a molecule that associates with a biological compound. A fluorescent organic dye is used to label a second biological compound or a second molecule that associates with a second biological compound. The QDs are constructed to emit light at a wavelength that corresponds to the excitation wavelength of the organic dye. Therefore in the presence of excitation light tuned to the excitation wavelength of the QDs and not the dye, when a first compound labeled with QDs is in close proximity (<100 Å) to a second compound labeled with an organic dye, the emission of the QDs will be absorbed by the dye resulting in excitation and fluorescence of the dye. Consequently, the color observed for this system will be the color of the fluorescent dye. If the first compound labeled with QDs is not in close proximity to a second compound labeled with an organic dye that absorbs light at the wavelength emitted by the QDs, the dye will not quench the emissions of the QDs. Thus, the color of the system will coincide with the color of the fluorescent QDs.

Figure 3:
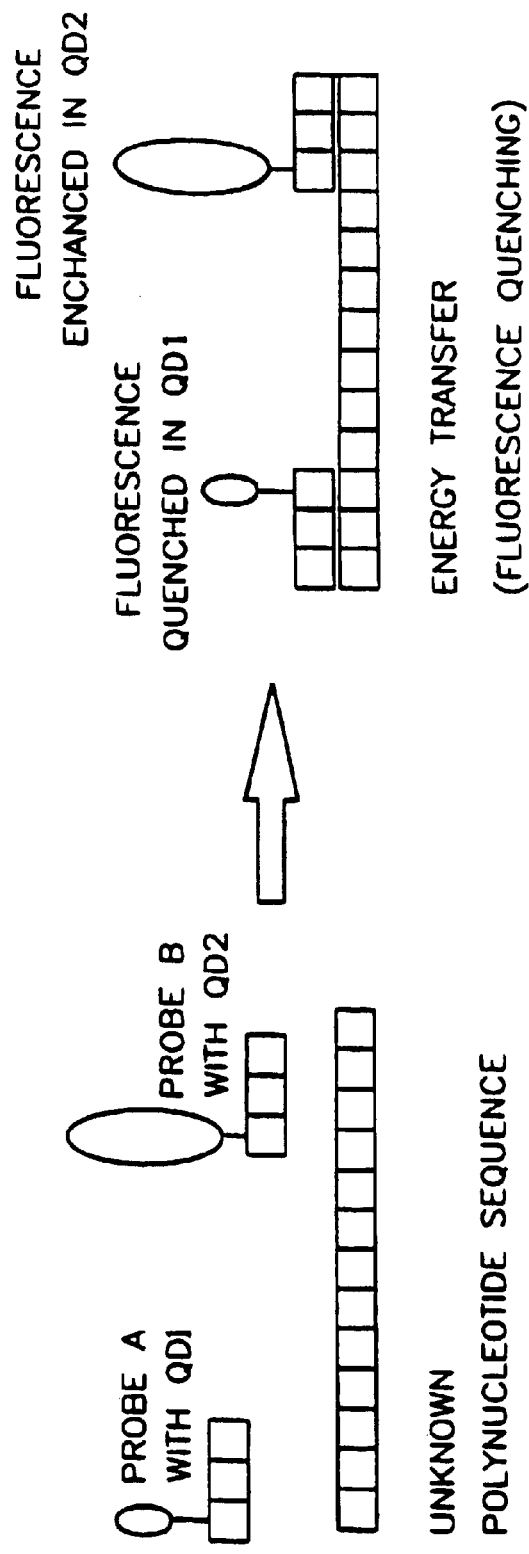
FIG. 3 is a cartoon depiction of the use of two differently colored QDs or one color QD and one organic dye to detect proximity of compounds. In this example, two oligonucleotide probes are hybridized to DNA sequences in close proximity and detected by fluorescence resonance energy transfer

As an example without limiting the scope of the invention, a first DNA probe is labeled with an organic fluorescent tag and hybridized to its target DNA sequence. A second DNA probe is labeled with QDs that are tuned to emit light corresponding to the excitation wavelength of the organic fluorescent tag. If the second probe hybridizes to a target sequence that is within at certain distance (<100 Å) to the first probe, in the presence of excitation light tuned to the QDs and not the dye, the fluorescent emission of the QDs will excite the organic dye and thus provide a signal (color of the dye) indicating proximity of the two sequences (FIG. 3). A signal indicating a lack of close proximity between the two probes would be the color of the QDs since the dye would not absorb the light emitted by the QDs and therefore would not fluoresce.

Alternatively, two different sized QD labels are attached to probe nucleotide sequences. If these strands bind to the target DNA, then the emissions from the smaller size dots should be quenched while those from the larger sized ones should be enhanced. Spectroscopic quantification of this energy transfer effect could be done in situ. Hence automated detection of sets of DNA sequences could also be realized.

In another preferred embodiment, a method of detecting proteases using FRET can be exploited. A peptide with a protease cleavage site is synthesized to contain a QD on one side of the cleavage site and an organic fluorescent dye on the other side in close proximity such that the emission of the QD is absorbed by the dye and thus quenched. In the presence of the protease, the peptide will be cleaved, releasing the two halves of the peptide and removing the quenching effect of the fluorescent dye. Therefore, detection of emitted light from the QD indicates that cleavage of the peptide by the protease.

Use of QDs in Flow Cytometry/Fluorescence Activated Cell Sorter (FACS)

In this method (see *Current Protocols in Cytometry* and *Current Protocols in Immunology*, John Wiley & Sons, Inc., New York; both of which are incorporated herein by reference), cells are labeled with a fluorescent dye and then passed, in a suspending medium, through a narrow dropping nozzle so that each cell is in a small droplet. A laser based detector system is used to excite fluorescence and droplets with positively fluorescent cells are given an electric charge. Charged and uncharged droplets are separated as they fall between charged plates and so collect in different tubes. The machine can be used either as an analytical tool, counting the number of labeled cells in a population or to separate the cells for subsequent growth of the selected population. Further sophistication can be built into the system by using a second laser system at right angles to the first to look at a second fluorescent label or to gauge cell size on the basis of light scatter. The utility of the method is that it looks at large numbers of individual cells and makes possible the separation of populations with, for example a particular surface properties.

QD technology can be applied to FACS. An advantage of using QDs in FACS is that using a single excitation light source, multiple components can be tagged. Therefore, cells may be sorted using a variety of parameters.

Diagnostics in Biological Applications

Quantum dot technology can be used in diagnostic systems for biological applications. Currently, the use of antibodies conjugated to fluorescent organic dyes for detection of biological moieties such as white blood cells and viruses (e.g. HIV) has limitations associated with the physical and spectral properties of these dyes. These limitations, as previously discussed, include the spectral overlap observed when using multiple dyes with different emission spectra which contributes to the background when using fluorescent-conjugated antibodies as a diagnostic assay. Thus, the present invention provides a method of detecting biological moieties as a diagnostic assay for medical purposes. In a preferred embodiment, QDs can be conjugated to molecules that are used to detect the presence and/or concentration of a biological compound for a diagnostic assay for medical purposes.

In a preferred embodiment, QDs can be conjugated to antibodies to detect components in blood or plasma such white blood cells, viruses (e.g. HIV), bacteria, cell-surface antigens of cancer cells, and any biological component associated with human diseases and disorders. As with previously described biological applications of the QD technology, the use of multiple QD allows the high-throughput screening of samples.

Imaging Apparatus

The present invention also provides an apparatus for reading the output of biological substrates encoded with multicolor fluorescent markers. An automated apparatus that detects multicolored luminescent biological systems can be used to acquire an image of the multicolored fluorescent system and resolve it spectrally. Without limiting the scope of the invention, the apparatus can detect samples by imaging or scanning. Imaging is preferred since it is faster than scanning. Imaging involves capturing the complete fluorescent data in its entirety. Collecting fluorescent data by scanning involves moving the sample relative to a microscope objective.

There are three parts to the apparatus: 1) an excitation source, 2) a monochromator to spectrally resolve the image, or a set of narrow band filters, and 3) a detector array. This apparatus can be applied to biological systems such as individual cells, a population of cells, or with an array of DNA.

In a preferred embodiment, for excitation of fluorescent markers, the apparatus would consist of a blue or ultraviolet light source for excitation of the QDs. Preferably, the wavelength of the light source is shorter than the wavelength of emissions of all QDs. As an example without limiting the scope of the invention since alternative methods may be used to obtain similar results, preferably, the light source is a broadband UV-blue light source such as a deuterium lamp with a filter attached to it. Another approach is to derive the light source from the output of a white light source such as a xenon lamp or a deuterium lamp and pass the light through a monochromator to extract out the desired wavelengths. Alternatively, filters could be used to extract the desired wavelengths.

In another preferred embodiment for the excitation of fluorescent markers, any number of continuous wave gas lasers can be used. These include, but are not limited to, any of the argon ion laser lines (e.g. 457, 488, 514 nm, etc.) or a HeCd laser. Furthermore, solid state diode lasers that have an output in the blue region of the spectrum such as GaN-based lasers or GaAs-based lasers with doubled output could be used. In addition, YAG or YLF-based lasers with doubled or tripled output, or any pulsed laser with an output also in the blue region can be used.

In a preferred embodiment, for the spectral resolution of the fluorescent QDs in a system, preferably the luminescence from the QDs is passed through an image-subtracting double monochromator. An alternative method of resolving the spectra of each QD in a system with multiple QDs is to pass the luminescent light through two single monochromators with the second one reversed from the first. The double monochromator consists of two gratings or two prisms and a slit between the two gratings. The first grating spreads the colors spatially. The slit selects a small band of colors and the second grating recreates the image. This image contains only the colors specific to the output of a QD of a particular size (emission).

In another preferred embodiment for resolving the emission spectra of a system containing multiple QDs is to use a computer-controlled color filter wheel where each filter is a narrow band filter centered at the wavelength of emission of one of the QDs in a system.

In a preferred embodiment, the fluorescent images are recorded using a camera preferably fitted with a charge-coupled device. Any two-dimensional detector can be used. Software is then used to color the images artificially to the actual wavelengths observed. The system then moves the gratings to a new color and repeats the process. The final output consists of a set of images of the same spatial region, each colored to a particular wavelength. This provides the necessary information for rapid analysis of the data.

In another preferred embodiment, an alternative method of detecting the fluorescent QDs in biological systems is to scan the samples. An apparatus using the scanning method of detection collects luminescent data from the sample relative to a microscope objective by moving either the sample or the objective. The resulting luminescence is passed thought a single monochromator, a grating or a prism to resolve the colors spectrally. Alternatively, filters could be used to resolve the colors spectrally.

For the scanning method of detection, the detector is a diode array which records the colors that are emitted at a particular spatial position. Software then recreates the scanned image, resulting in a single picture (file) containing all the colors of the QDs in the sample.

Since an entire spectrum is captured in a single file, in systems with multiple QDs, spectral deconvolution is necessary and easily performed to resolve overlapping spectra. As previously discussed, the narrow spectral linewidths and nearly gaussian symmetrical lineshapes lacking a tailing region observed for the emission spectra of QDs combined with the tunability of the emission wavelengths of QDs allows high spectral resolution in a system with multiple QDs. In theory, up to 10–20 different-sized QDs from different preparations of QDs, with each sample having a different emission spectrum, can be used simultaneously in one system with the overlapping spectra easily resolved using deconvolution software.

Photoluminescence of Single Nanocrystal Quantum Dots

Single nanocrystal quantum dots have detectable luminescence (Nirmal et al. *Nature* 383: 802, 1996; and Empedocles et al. *Phys. Rev. Lett.* 77:3873, 1996; both incorporated herein by reference) which can be applied to biological systems. An advantage of having highly fluorescent single QDs that are detectable and associated with biological compounds is that this allows the detection of very small quantities of biological molecules. Thus, the throughput of assays that screen large numbers of samples can be improved by utilizing single QDs associated with biological compounds to decrease the sample size, and consequently allowing a greater number of samples to be screen at any one time.

The following Examples illustrate the preferred modes of making and practicing the present invention, but are not meant to limit the scope of the invention since alternative methods may be used to obtain similar results.

EXAMPLES

Example 1

Preparation of TOPO Capped-(CdSe)ZnS (a) Preparation of CdSe Trioctylphosphine oxide (TOPO, 90% pure) and trioctylphosphine (TOP, 95% pure) were obtained from Strem and Fluka, respectively. Dimethyl cadmium ($CdMe_2$) and diethyl zinc ($ZnEt_2$) were purchased from Alfa and Fluka, respectively, and both materials were filtered separately through a 0.2:m filter in an inert atmosphere box. Trioctylphosphine selenide was prepare by dissolving 0.1 mols of Se shot in 100 ml of TOP thus producing a 1M solution of TOPSe. Hexamethyl (disilathiane) ($TMS_2S$) was used as purchased from Aldrich. HPLC grade n-hexane, methanol, pyridine and n-butanol were purchased from EM Sciences.

The typical preparation of TOP/TOPO capped CdSe nanocrystals follows. TOPO (30 g) was placed in a flask and dried under vacuum (~1 Torr) at 180° C. for 1 hour. The flask was then filled with nitrogen and heated to 350° C. In an inert atmosphere drybox the following injection solution was prepared: $CdMe_2$ (200 microliters, 2.78 mmol), 1 M TOPSe solution (4.0 mL, 4.0 mmol), and TOP (16 mL). The injection solution was thoroughly mixed, loaded into a syringe, and removed from the drybox.

The heat was removed from the reaction flask and the reagent mixture was delivered into the vigorously stirring TOPO with a single continuous injection. This produces a deep-yellow/orange solution with a sharp absorption feature at 470–500 nm and a sudden temperature decrease to ~240° C. Heating was restored to the reaction flask and the temperature was gradually raised to 260–280° C.

Aliquots of the reaction solution were removed at regular intervals (5–10 min) and absorption spectra taken to monitor the growth of the crystallites. The best samples were prepared over a period of a few hours steady growth by modulating the growth temperature in response to changes in the size distribution, as estimated from the sharpness of the features in the absorption spectra. The temperature was lowered 5–10° C. in response to an increase in the size distribution. Alternatively, the reaction can also be stopped at this point. When growth appears to stop, the temperature is raised 5–10° C. When the desired absorption characteristics were observed, the reaction flask was allowed to cool to ~60° C. and 20 mL of butanol were added to prevent solidification of the TOPO. Addition of a large excess of methanol causes the particles to flocculate. The flocculate was separated from the supernatant liquid by centrifugation; the resulting powder can be dispersed in a variety of organic solvents (alkanes, ethers, chloroform, tetrahydrofuran, toluene, etc.) to produce an optically clear solution.

(b) Preparation of (CdSe)ZnS A flask containing 5 g of TOPO was heated to 190 EC under vacuum for several hours then cooled to 60 EC after which 0.5 mL trioctylphosphine (TOP) was added. Roughly 0.1–0.4:mols of CdSe dots dispersed in hexane were transferred into the reaction vessel via syringe and the solvent was pumped off.

Diethyl zinc ($ZnEt_2$) and hexamethyldisilathiane (($TMS)_2S$) were used as the Zn and S precursors, respectively. The amounts of Zn and S precursors needed to grow a ZnS shell of desired thickness for each CdSe sample were determined as follows: First, the average radius of the CdSe dots was estimated from TEM or SAXS measurements. Next, the ratio of ZnS to CdSe necessary to form a shell of desired thickness was calculated based on the ratio of the shell volume to that of the core assuming a spherical core and shell and taking into account the bulk lattice parameters of CdSe and ZnS. For larger particles the ratio of Zn to Cd necessary to achieve the same thickness shell is less than for the smaller dots. The actual amount of ZnS that grows onto the CdSe cores was generally less than the amount added due to incomplete reaction of the precursors and to loss of some material on the walls of the flask during the addition.

Equimolar amounts of the precursors were dissolved in 2–4 mL TOP inside an inert atmosphere glove box. The precursor solution was loaded into a syringe and transferred to an addition funnel attached to the reaction flask. The reaction flask containing CdSe dots dispersed in TOPO and TOP was heated under an atmosphere of $N_2$. The temperature at which the precursors were added ranged from 140° C. for 23 Å diameter dots to 220° C. for 55 Å diameter dots. When the desired temperature was reached the Zn and S precursors were added dropwise to the vigorously stirring reaction mixture over a period of 5–10 minutes.

After the addition was complete the mixture was cooled to 90° C. and left stirring for several hours. Butanol (5 mL) was added to the mixture to prevent the TOPO from solidifying upon cooling to room temperature. The overcoated particles were stored in their growth solution to ensure that the surface of the dots remained passivated with TOPO. They were later recovered in powder form by precipitating with methanol and redispersing into a variety of solvents including hexane, chloroform, toluene, THF and pyridine.

Example 2

Preparation of a Water-Soluble Quantum Dots Using Long Chain Mercaptocarboxylic Acid TOPO capped-(CdSe)ZnS quantum dots were prepared as described in Example 1. The overcoated (CdSe)ZnS dots were precipitated from the growth solution using a mixture of butanol and methanol. To obtain the precipitated quantum dots, the solution was centrifuged for 5–10 min, the supernatant was decanted and the residue was washed with methanol (2×).

The residue was weighed. The weight of the TOPO cap was assumed to be 30% of the total weight; and a 30-fold molar excess of the new capping compound, 11-mercaptoundecanoic acid (MUA) was added. The residue and MUA (neat solution) were stirred at 60° C. for 8–12 hours. A volume of tetrahydrofuran (THF) equal to the added MUA was added to the MUA/dot mixture, with the mixture was still hot. A clear solution resulted and the coated quantum dots were stored under THF.

Figure 4:
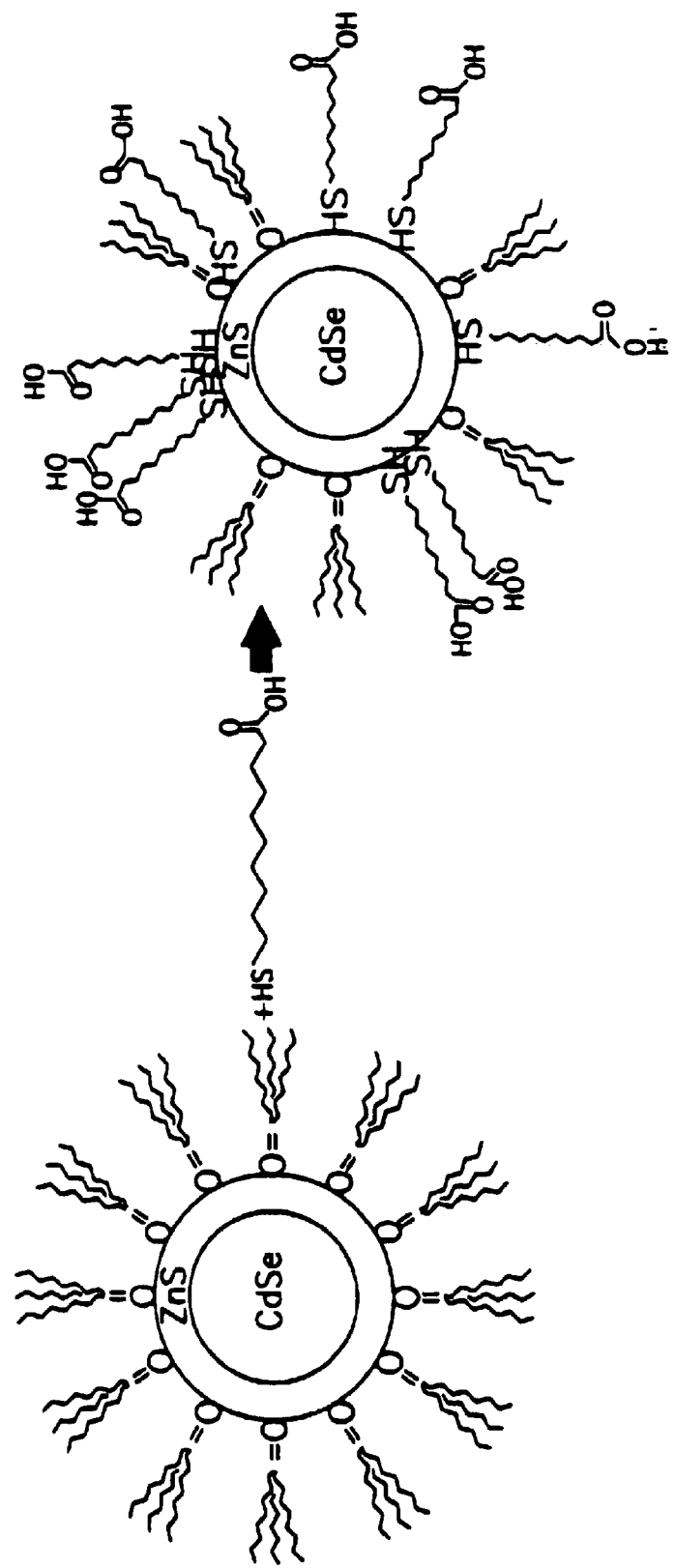
FIG. 4 is a cartoon depiction of the formation of water-soluble quantum dots by cap exchange FIG. 5 outlines the reaction between biotin and hexane dithiol to form the biotin-hexane dithiol (BHDT) derivative.

The coated quantum dots are rendered water-soluble by deprotonation of the carboxylic acid functional group of the MUA (FIG. 4). The deprotonation was accomplished by adding a suspension of potassium t-butoxide in THF to the MUA-quantum dot/THF solution. A gel resulted, which was then centrifuged and the supernatant liquid was poured off. The residue was washed twice with THF, centrifuged each time and the supernatant liquid poured off. The final residue was allowed to dry in air for 10 minutes. Deionized water (Millipore) was added to the residue until a clear solution formed.

The resultant coated quantum dots were tested for photoluminescent quantum yield. A CdSe quantum dot with a four monolayer coating of ZnS coated as described had an absorption band a 480 nm and a photoluminescent band at 500 nm, with a quantum yield of 12%. A second CdSe quantum dot with a four monolayer coating of ZnS coated as described had an absorption band a 526 nm and a photoluminescent band at 542 nm, with a quantum yield of 18%.

Example 3

Associating a Water-Solubilzed Quantum Dot with a Protein

CdSe quantum dots overcoated with ZnS were synthesized, purified, and solubilized in water as previously described. Samples used in this experiment had 40 Å diameter CdSe cores, a ZnS shell which was nominally 4 monolayers (about 9 Å) thick, and capped with 11-mercaptoundecanoic acid (MUA).

The following three reagents were mixed: 5.8 mg of 1-ethyl-3-(3-dimethylaminopropyl) carbodiimide hydrochloride (EDAC), 2.4 mg of N-hydroxysuccinimide (NHS), and 4 mL of a 0.82 micromolar solution of avidin in Millipore filtered water. The initially acidic mixture was treated with 0.1 M NaOH (aq) to adjust the pH to 7.6. Then 3 mL of a 2.1 micromolar aqueous solution of (CdSe)ZnS quantum dots was added. The mixture was stirred for 1 hour at room temperature. Excess reagents were quenched with 1 drop of 0.25 M ethanolamine in water.

To determine whether avidin coupling was successful, the colored reaction solution was passed through a short column containing biotin-coated acrylic beads. The filtrate which emerged was nearly colorless. The column was then washed with 10-fold volume of water. Under excitation with ultraviolet light, the beads displayed strong fluorescence due to the bound quantum dots, indicating successful coupling to avidin. A control experiment using only quantum dots and avidin with reagents to couple them (i.e. no EDAC or NHS) produced beads with little or no fluorescence, confirming that without avidin-coupling the quantum dots do not bind to the biotin coated beads.

Example 4

Biotin Hexane Dithiol (BHDT) Formation

Figure 5:
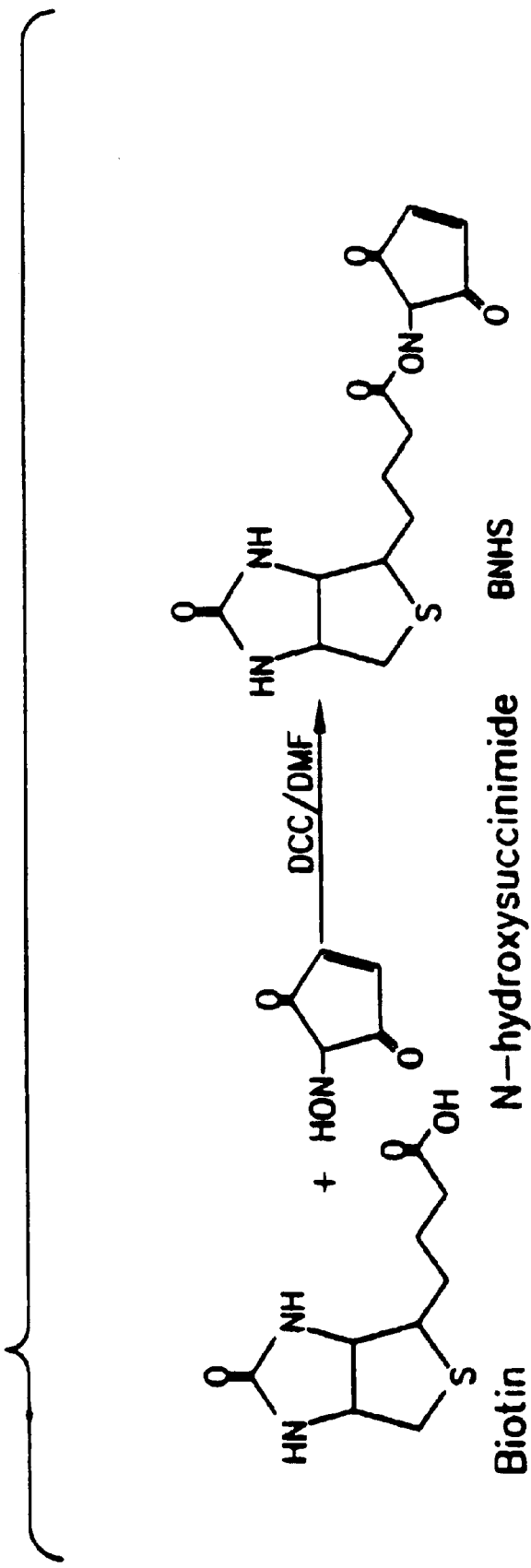

This procedure exploits the activated carboxylic acid group present in the biotin derivative, biotin-N-hydroxysuccinimide (BNHS; Pierce Chemicals, Rockford, Ill.) to made a biotin derivative which terminates in a thiol (SH) group (FIG. 5). The presence of a thiol group is desired because thiols, in general, tend to adsorb to metal surfaces. Therefore, the thiol linkage can be exploited to attach biotin to the water-soluble quantum dots.

BNHS was dissolved in DMF and a 10-fold excess of 1,6-hexanedithiol was added in the presence of a weak base (triethylamine). The solution was stirred at room temperature for 16 hours. An NHS precipitate results and the solution was filtered to remove this NHS precipitate. The precipitate was washed with DMF. The precipitate was reduced to a minimum volume by removing solvent under a vacuum. Ether was then added to the concentrated solution to precipitate crude product. The product was isolated by filtration and the residue was pumped under a vacuum to remove the excess dithiol. A white powder (BHDT) was isolated and stored in the glove-box refrigerator to prevent thiol oxidation into disulfide. The resultant yield was approximately 68%.

Example 5

Biotin-Amine Formation

Figure 6:
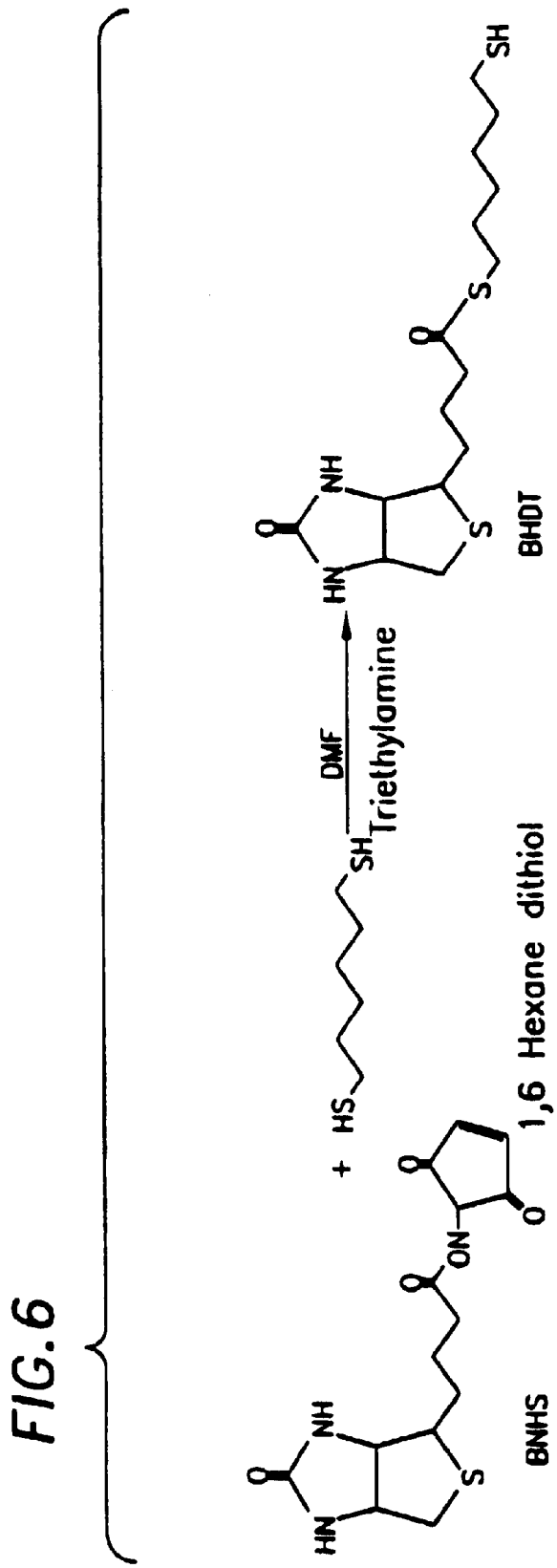
FIG. 6 outlines the reaction between biotin and a diamine to form biotin-amine derivative.

The philosophy of this procedure is similar to the one described in Example 6. In this example, the activated carboxylic group in biotin is utilized to make a biotin derivative with a terminal amine group (FIG. 6). As with thiols, amines conjugate to metal surfaces and can be used to attach biotin to the dots.

100 mg of BNHS was added to 2 ml DMF in a vial and mixed until all the BNHS had dissolved. Next, 0.9 ml of 1,3 diaminopropane (a 30 fold excess) was added to another vial. The BNHS/DMF solution was pipetted into the vial containing the neat 1,3-diaminopropane in 2 aliquots. The additions were performed in approximately 2 minutes and were spaced by 5 minutes. The resulting solution was stirred at room temperature for 24 hours, and a white precipitate (NHS) was formed. The NHS precipitate was removed by centrifuging, and the clear supernatant was transferred to another vial. Excess ether was added to the supernatant. Upon shaking, an immiscible layer was formed at the bottom which was transferred to a round-bottomed flask. DMF and excess diamine were then removed under vacuum to yield a white powder. The resultant yield was approximately 72%.

Example 6

Biotin-Thiol-Dot Complex Formation

Figure 7:
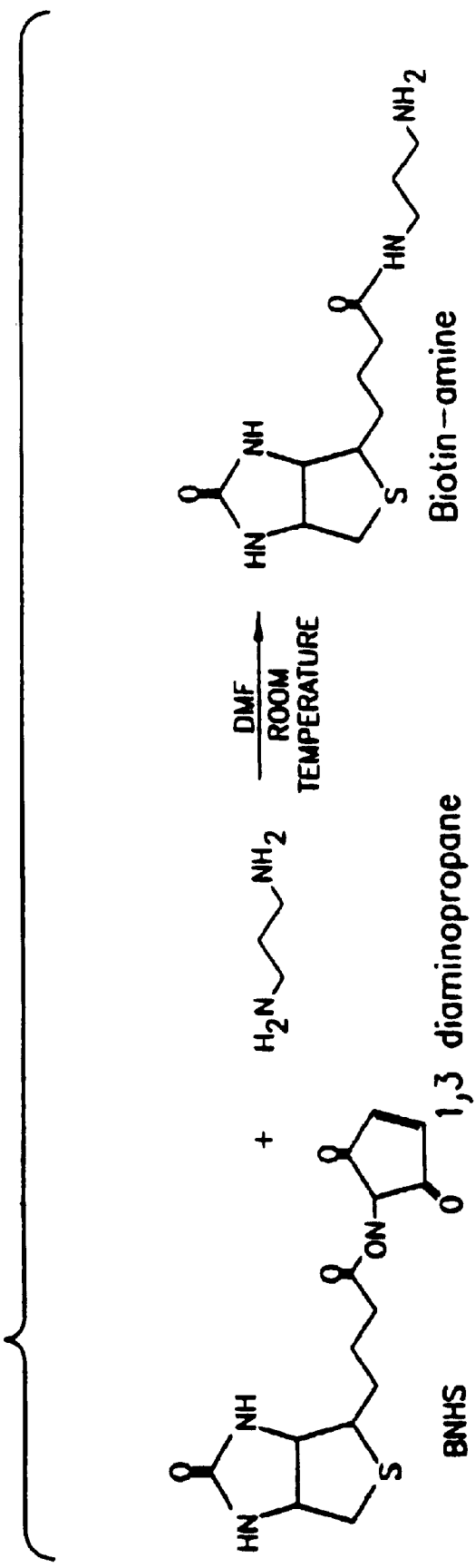
FIG. 7 depicts the formation of the biotin-thiol-dot complex for a water-soluble dot.

The aim of this protocol is to attach a biotin cap onto the surface of the dots. The thiol end group of BHDT should adsorb to the dot surface (FIG. 7). Excess MUA from the cap was removed from the quantum dot/THF solution by precipitating the dots with a hexane/butanol mixture. The precipitate was redispersed in DMF and then precipitated again with a hexane/BuOH mixture. The precipitate was allowed to dry in air for 20–25 minutes, weighed, and redissolved in DMF. To calculate the amount of BHDT to dissolve in DMF, it was estimated that 30% of the total weight of the dot was derived from the cap. With that estimation, a 10-fold excess of BHDT (relative to the cap) was dissolved in DMF in a separate vial. The BHDT solution was then added to the QD/DMF solution over a 5 minute period. This mixture was stirred at room temperature for approximately 15 hours. The reaction was stopped by centrifugation, saving only the supernatant. A solution of potassium tert-butoxide in DMF was used to deprotonate the MUA acid cap. A colored precipitate was formed which is the water-soluble product. This mixture was subjected to centrifugation and the clear supernatant was discarded. No photoluminescence was observed from this layer indicating that all QDs were successfully precipitated out of solution.

The precipitate was dissolved in deionized $H_2O$ (Millipore; Bedford, Mass.). The resulting solution was filtered through a 0.2 μm filter (Millipore), and transferred to a Ultrafree-4™ concentrator (Millipore). The solution was spun three times through the concentrator, and after each spin, the tubes were topped off with water. The concentrated solution was transferred to a vial and diluted with water. To confirm that biotin was successfully conjugated to the dots, the resulting solution was passed over an immobilized avidin column (Ultra-link™, Pierce, Rockford, Ill.). Dots derivatized with biotin were retained by the column, resulting in the fluorescence of the column when illuminated with a UV-lamp. Control columns, which had non-biotinylated dots passed over them, showed no fluorescence when illuminated with a UV lamp

Example 7

Biotin-Amine-Dot Complex Formation

Figure 8:
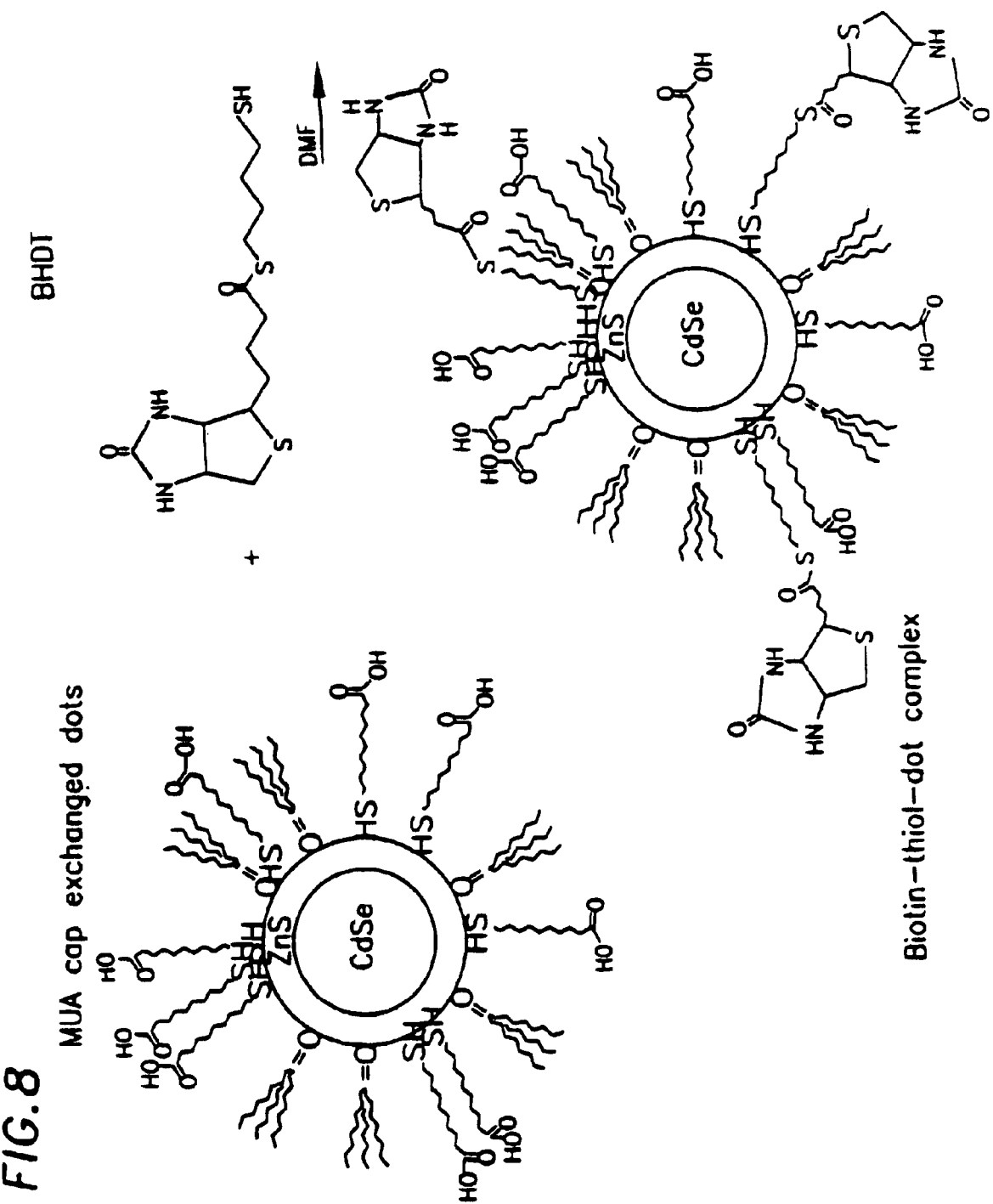
FIG. 8 depicts the formation of the biotin-amine-dot complex where the amine is adsorbed to the outer layer of the dot.

This protocol allows one to attach biotin to the surface of the dots. Conjugation of biotin to the dots is achieved through the primary amine group at the end of biotin. Again, the affinity of the amine group for the surface of the dot is being exploited in this protocol (FIG. 8).

In this protocol, the MUA capped dots were precipitated from the QD/THF solution using a hexane/BuOH mixture. The dots were air-dried for approximately 5 minutes and weighed. Deprotonation of the dots was accomplished by adjusting the pH of the solution to 10.5 with a 1M solution of $NH_4OH$. To calculate the amount of excess biotin-amine to use, it was estimated that 30% of the overall weight of the dots was derived from the cap. As such, a 10-fold excess (to the cap) of the biotin-amine reagent that was previously synthesized as in Example 5 was weighed out in a separate vial. This biotin derivative was then dissolved in a minimum volume of water. The solution containing the biotin-amine conjugate was pipetted into the solution of deprotonated dots over the course of about 3 minutes, and then stirred at room temperature for approximately 12 hours. The reaction was stopped by centrifugation, and the resulting supernatant was passed through a 0.2 $\mu$m filter (Millipore).

After filtration, the solution was transferred to a Ultrafree-4™ concentrator (Millipore; MW cutoff=30 kDa). The solution was spun three times through the concentrator, and after each spin, the tubes were topped off with deionized water. The final concentrated solution was diluted again with water and refiltered through a 0.2 $\mu$m filter. The resulting clear solution was passed over an immobilized avidin column (Ultra-link™ matrix; Pierce) to confirm biotinylation of the dots as described in Example 6.

Example 8

Biotin-Amine-Dot Complex Formation (Alternate Route)

Figure 9:
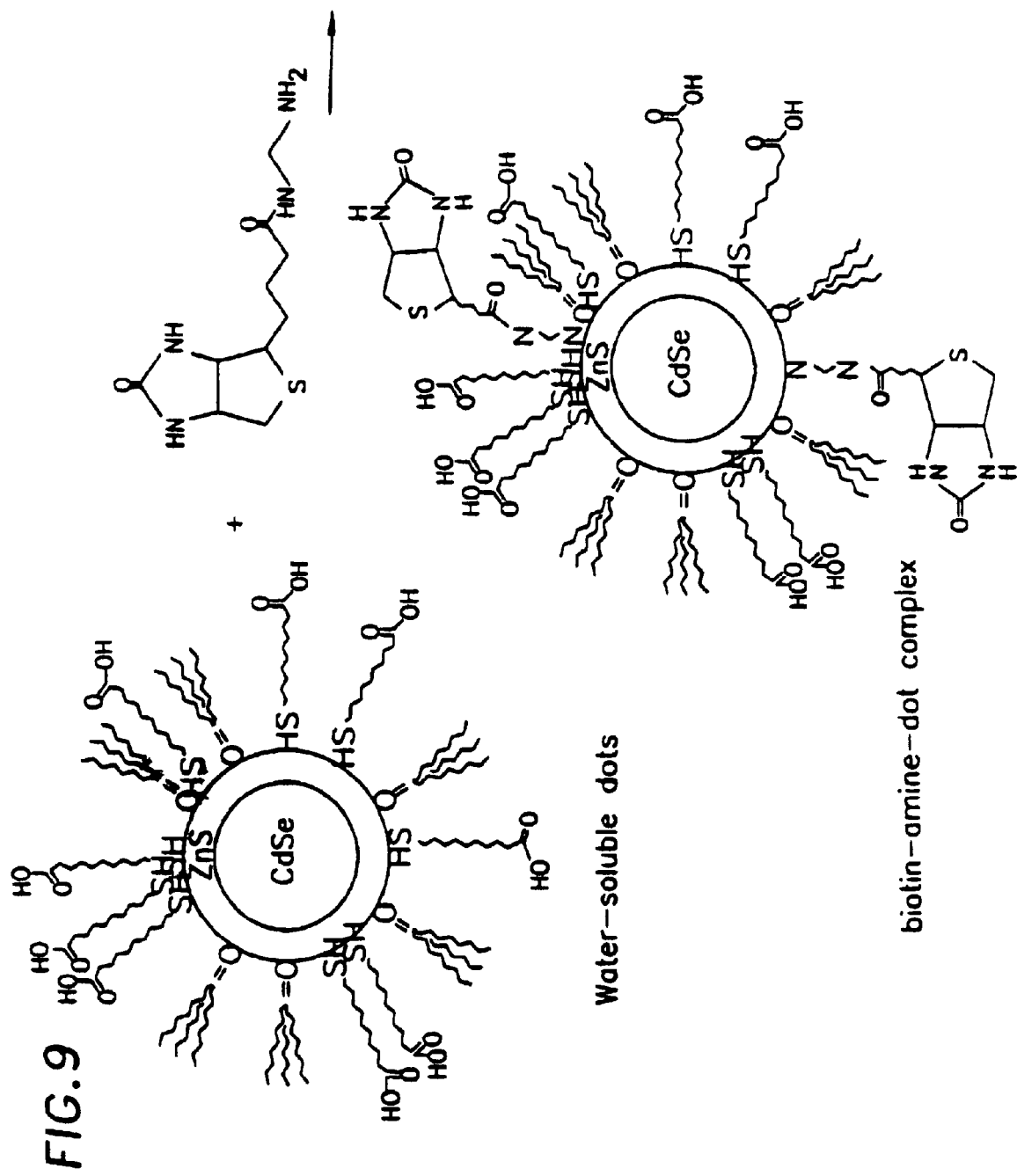
FIG. 9 depicts the formation of the biotin-amine-dot complex where the amine is conjugated to the carboxylic acid group of the water-solubilizing later.

Unlike the procedures described in the previous Examples, this protocol utilizes the carboxylic acid groups that cap the surface of the water-soluble dots described in Example 2 (see FIG. 9). An amide bond is formed by conjugating a biotin-primary amine derivative to the carboxylic acid group at the surface of the dots. This coupling is done with the aid of 1-ethyl-3-(3-dimethylaminopropyl) carboimide hydrochloride (EDC; Pierce Chemicals, MW=191.7 g/mol), another group that activates the carboxylic acid group for use in subsequent reactions.

The MUA-capped dots dissolved in THF were precipitated by deprotonating the carboxylic acid group. This deprotonation was accomplished by adding a potassium tert-butoxide/THF suspension. The resulting residue was washed with THF twice, air-dried for 10–15 minutes, and weighed. Deionized water was then added to the residue and the suspension was shaken until the residue was completely dissolved. An aliquot from this solution was then concentrated by centrifugation three times using an Ultrafree-4™ concentrator (Millipore). Again, after each concentration, the tube was topped off with Millipore filtered water. The pH of the solution was adjusted to 9 using a 1M solution of $NH_4OH$.

For the following calculations, the weight of the acid cap was assumed to be 30% of the total weight of the dots. A solution of EZ-Link™ biotin-PEO-LC-Amine (Pierce Chemicals, MW=418 g/mol) and (1-ethyl-3-(3-dimethylaminopropyl) carboimide hydrochloride (EDC) in water at a molar equivalent of 1:1 (biotin derivative:acid cap) and 10:1 (EDC:acid cap) was then added to the dots (pH=8.5). This mixture was stirred at room temperature for 2–3 hours. The reaction was stopped by filtering the solution through a 0.2 $\mu$m Millipore filter twice.

As in Example 6, conjugation of biotin to the dots was confirmed by passing the sample over an avidin column. Successful conjugation resulted in a fluorescent column. A control column with non-biotinylated dots passed over it did not fluoresce.

Example 9

Quantum Dot-Oligonucleotide Complex Formation

This procedure is derived from the synthesis of the biotin-amine-dot complex. In particular, molar equivalents used in Example 5 will be used to complex the quantum dots to 5' amine-labeled oligonucleotides.

A solution of MUA-capped dots dissolved in THF will be deprotonated using potassium tert-butoxide. The resulting gel will be washed with THF twice, centrifuged, and the subsequent supernatant discarded. The final residue is air-dried and weighed. Deionized water is added to the dried residue and shaken until a clear solution results. An aliquot of the solution is desalted and concentrated twice using an Ultrafree-4™ concentrator (Millipore). After each concentration, the concentrator tube is topped off with deionized water.

The amount of dots is estimated from the ratio of volumes of the aliquot and the total volume of water used. Relative to the amount of dots, one molar equivalent of 5' amine-labeled oligonucleotide and 10 molar equivalents of EDC (Pierce, mol wt=192) are dissolved in water. The pH of this solution is adjusted to 8.5. This solution is then added to the solution of dots described in the preceding section and stirred at room temperature for 2–3 hours. The reaction is stopped by passing the solution through 0.2 $\mu$m Millipore filter, and concentrating the filtrate using an Ultrafree-4™ concentrator.

Conjugation of the dots to the oligonucleotide will be checked using a protocol described in the next Example.

Example 10

Quantum Dot-Oligonucleotide Complex Formation Check

The same column used to confirm biotin-dot formation can be modified to check for oligo-dot complex formation. A solution of 5' biotin-labeled oligonucleotide, complementary in sequence to the oligonucleotide complexed with the dots, will be passed through an Ultra-link™ (Pierce Chemicals) immobilized avidin column. The biotin will bind to the avidin to form an immobilized, oligonucleotide column. The oligonucleotide-dot conjugation will then be checked by passing the solution of the oligonucleotide-dot complex over this column. Complementary DNA sequences will be allowed to hybridize at the appropriate hybridization temperature for 12 hours as calculated by standard methods (Sambrook et al., *Molecular Cloning: A Laboratory Manual*, Cold Spring Harbor Laboratory Press, Cold Spring Harbor, N.Y., 1989; incorporated herein by reference). After hybridization, the column will be washed with water to remove any unbound oligonucleotide-dots complexes. Successful oligonucleotide-dot conjugation and subsequent hybridization to the complementary oligonucleotide column should result in a column that fluoresces with the appropriate excitation light. No fluorescence suggests all the color disappeared upon elution and that no complex was formed between the dots and the oligonucleotide.

What is claimed is:

1. A method of detecting biological moieties comprising:
   providing a plurality of compositions capable of characteristic spectral emissions, the composition comprising a compound and a semiconductor nanocrystal associated with the compound, wherein each of the members of the plurality is characterized in that:
      the nanocrystal of the member of the plurality has an emission spectrum distinct from the other members of the plurality and a quantum yield of greater than 10% in water, and
      the compound of the member of the plurality has a corresponding biological moiety distinct from other biological moieties in the sample;
   allowing a sample containing or suspected of containing one or more biological moieties to interact with the compositions; and
   monitoring the spectral emission of each interaction between each composition and each biological moiety of the sample, wherein the interaction between the biological moiety and the composition comprises a noncovalent interaction.

2. The method of claim 1, wherein the compound comprises a molecular complex with a molecule associated with the nanocrystal complexed to a second molecule that interacts with the biological moiety.

3. The method of claim 1, wherein each interaction between each composition and each biological moiety of the sample are monitored substantially simultaneously.

4. The method of claim 1, wherein the spectral emission provides information about a biological state or event.

5. The method of claim 4, wherein the spectral emission provides information about the amount of biological moiety in the sample.

6. The method of claim 4, wherein the spectral emission provides information about the presence of the biological moiety in the sample.

7. The method of claim 1, wherein the semiconductor nanocrystal is water-soluble.

8. The method of claim 1, wherein the semiconductor nanocrystal comprises a core comprising a semiconductor material, and a layer overcoating the core comprising a semiconductor material.

9. The method of claim 1, wherein the spectral emission is tunable to a desired wavelength by controlling the size of the nanocrystal.

10. The method of claim 1, wherein monitoring the spectral emission occurs in assays selected from the group consisting of:
   immunochemistry, immunocytochemistry, immunobiology, immunofluorescence, DNA sequence analysis, fluorescence resonance energy transfer, flow cytometry, fluorescence activated cell sorting, diagnostics in biological systems, and high-throughput screening.

11. The method of claim 1, wherein the noncovalent interaction comprises hydrophobic interaction, hydrophilic interaction, electrostatic interaction, van der Waals interaction, or magnetic interaction.

12. The method of claim 1, wherein the biological moiety comprises a small molecule.

13. The method of claim 1, wherein the biological moiety comprises a protein, peptide or antibody.

14. The method of claim 1, wherein the biological moiety comprises a nucleic acid.

15. The method of claim 14, wherein the nucleic acid comprises DNA or RNA.

16. The method of claim 1, wherein the biological moiety comprises an amino acid.

17. The method of claim 1, wherein the biological moiety comprises a ligand.

18. The method of claim 1, wherein the biological moiety comprises an antigen.

19. The method of claim 1, wherein the biological moiety comprises a cell.

20. The method of claim 1, wherein the biological moiety comprises a subcellular organelle.

21. A method of detecting biological moieties comprising:
   providing a plurality of compositions capable of characteristic spectral emissions, the composition comprising a compound and a semiconductor nanocrystal associated with the compound, wherein each of the members of the plurality is characterized in that:
      the nanocrystal of the member of the plurality has an emission spectrum distinct from the other members of the plurality, and
      the compound of the member of the plurality has a corresponding biological moiety distinct from other biological moieties in the sample and is associated with the nanocrystal by a ligand having at least one linking group for attachment to the nanocrystal spaced apart from a hydrophilic group by an alkyl or alkenyl group;
   allowing a sample containing or suspected of containing one or more biological moieties to interact with the compositions; and
   monitoring the spectral emission of each interaction between each composition and each biological moiety of the sample, wherein the interaction between the biological moiety and the composition comprises a noncovalent interaction.

22. The method of claim 21, wherein the hydrophilic group is selected from the group consisting of carboxylic acid, carboxylate, sulfonate, hydroxide, alkoxide, ammonium, phosphate, and phosphonate.

23. The method of claim 21, wherein each interaction between each composition and each biological moiety of the sample are monitored substantially simultaneously.

24. The method of claim 21, wherein the spectral emission provides information about a biological state or event.

25. The method of claim 21, wherein the semiconductor nanocrystal is water-soluble.

26. The method of claim 21, wherein the semiconductor nanocrystal comprises a core comprising a semiconductor material, and a layer overcoating the core comprising a semiconductor material.

27. The method of claim 21, wherein the biological moiety comprises a small molecule.

28. The method of claim 21, wherein the biological moiety comprises a protein, peptide or antibody.

29. The method of claim 21, wherein the biological moiety comprises a nucleic avid.

30. The method of claim 29, wherein the nucleic acid comprises DNA or RNA.

31. The method of claim 21, wherein the biological moiety comprises an amino acid.

32. The method of claim 21, wherein the biological moiety comprises a ligand.

33. The method of claim 21, wherein the biological moiety comprises an antigen.

34. The method of claim 21, wherein the biological moiety comprises a cell.

35. The method of claim 21, wherein the biological moiety comprises a subcellular organelle.

36. The method of claim 21, wherein the spectral emission is tunable to a desired wavelength by controlling the size of the nanocrystal.

37. The method of claim 21, wherein monitoring the spectral emission occurs in assays selected from the group consisting of:

immunochemistry, immunocytochemistry, immunobiology, immunofluorescence, DNA sequence analysis, fluorescence resonance energy transfer, flow cytometry, fluorescence activated cell sorting, diagnostics in biological systems, and high throughput screening.

38. The method of claim 21, wherein the spectral emission is tunable to a desired wavelength by controlling the size of the nanocrystal.

39. The method of claim 21, wherein monitoring the spectral emission occurs in assays selected from the group consisting of:

immunochemistry, immunocytochemistry, immunobiology, immunofluorescence, DNA sequence analysis, fluorescence resonance energy transfer, flow cytometry, fluorescence activated cell sorting, diagnostics in biological systems, and high throughput screening.

40. The method of claim 21, wherein the noncovalent interaction comprises hydrophobic interaction, hydrophilic interaction, electrostatic interaction, van der Waals interaction, or magnetic interaction.

* * * * *